(12) United States Patent
Acosta et al.

(10) Patent No.: US 10,047,273 B2
(45) Date of Patent: Aug. 14, 2018

(54) BETA-AMINO ESTER GAS HYDRATE INHIBITORS

(71) Applicant: Nalco Company, Naperville, IL (US)

(72) Inventors: Erick J. Acosta, Sugar Land, TX (US); Tran-Bich Cao, Houston, TX (US)

(73) Assignee: Ecolab USA Inc., St. Paul, MN (US)

( * ) Notice: Subject to any disclaimer, the term of this patent is extended or adjusted under 35 U.S.C. 154(b) by 332 days.

(21) Appl. No.: 15/111,443

(22) PCT Filed: Dec. 20, 2013

(86) PCT No.: PCT/US2013/077326
§ 371 (c)(1),
(2) Date: Jul. 13, 2016

(87) PCT Pub. No.: WO2014/105764
PCT Pub. Date: Jul. 3, 2014

(65) Prior Publication Data
US 2016/0362595 A1    Dec. 15, 2016
US 2017/0190947 A9    Jul. 6, 2017

Related U.S. Application Data

(60) Provisional application No. 61/746,857, filed on Dec. 28, 2012.

(51) Int. Cl.
| | | |
|---|---|---|
| *C09K 8/52* | (2006.01) | |
| *C08G 65/00* | (2006.01) | |
| *C07D 295/15* | (2006.01) | |
| *C07D 295/088* | (2006.01) | |
| *C10L 1/232* | (2006.01) | |
| *C10L 1/233* | (2006.01) | |
| *C10L 1/2387* | (2006.01) | |
| *C10L 1/24* | (2006.01) | |
| *C10L 3/10* | (2006.01) | |

(52) U.S. Cl.
CPC ............ *C09K 8/52* (2013.01); *C07D 295/088* (2013.01); *C07D 295/15* (2013.01); *C08G 65/00* (2013.01); *C10L 1/232* (2013.01); *C10L 1/233* (2013.01); *C10L 1/2387* (2013.01); *C10L 1/2462* (2013.01); *C10L 1/2475* (2013.01); *C10L 3/107* (2013.01); *C09K 2208/22* (2013.01); *C10L 2230/14* (2013.01)

(58) Field of Classification Search
None
See application file for complete search history.

(56) References Cited

U.S. PATENT DOCUMENTS

| | | | | |
|---|---|---|---|---|
| 3,167,554 | A * | 1/1965 | Ernst | C07D 295/13 106/14.16 |
| 4,125,636 | A | 11/1978 | Kamio et al. | |
| 4,557,838 | A * | 12/1985 | Nichols | C09K 8/54 252/390 |
| 5,883,210 | A * | 3/1999 | Ahmed | C07C 237/04 526/263 |
| 8,105,987 | B2 * | 1/2012 | Acosta | C07D 241/04 106/14.16 |
| 8,105,988 | B2 * | 1/2012 | Acosta | C09K 8/54 106/14.16 |
| 2012/0078021 | A1 | 3/2012 | Durham et al. | |
| 2012/0190846 | A1 | 7/2012 | Fabian et al. | |
| 2014/0106991 | A1 * | 4/2014 | Acosta | C09K 8/52 507/90 |

FOREIGN PATENT DOCUMENTS

| | | | |
|---|---|---|---|
| WO | 2010/104727 A1 | 9/2010 | |
| WO | WO 2010104727 A1 * | 9/2010 | ........... C07D 241/04 |
| WO | 2012/082815 A2 | 6/2012 | |

OTHER PUBLICATIONS

PubChemCompound, datasheet [online compound summary] Retrieved from the Internet: http://pubchem.ncbi.nlm.nih.gov/search/search.cgi. See CID 57994398, 6 pages (no date).
International Search Report dated Apr. 14, 2014 relating to PCT Application No. PCT/US2013/077326, 4 pages.
Written Opinion dated Apr. 14, 2014 relating to PCT Application No. PCT/US2013/077326, 7 pages.
Extended European Search Report dated Jul. 12, 2016 relating to European Application No. 13867429.6, 8 pages.

* cited by examiner

*Primary Examiner* — John J Figueroa
(74) *Attorney, Agent, or Firm* — Senniger Powers LLP

(57) ABSTRACT

Disclosed herein are beta-amino ester surfactant compounds and compositions useful in applications relating to inhibition of gas hydrate agglomerates in the production, transportation, storage, and separation of crude oil and natural gas. Also disclosed herein are methods of using the compounds and compositions as gas hydrate inhibitors, particularly in applications relating to the production, transportation, storage, and separation of crude oil and natural gas.

20 Claims, No Drawings

BETA-AMINO ESTER GAS HYDRATE INHIBITORS

CROSS-REFERENCE TO RELATED APPLICATIONS

This application is a U.S. National Patent Application of PCT/US2013/077326, filed Dec. 20, 2013 which claims the benefit of U.S. Provisional Application Ser. No. 61/746,857 which was filed Dec. 28, 2012. The entire content of these applications is incorporated herein by reference.

TECHNICAL FIELD

The present disclosure relates generally to low dosage hydrate inhibitors, and more particularly to beta-amino ester surfactants for the inhibition of gas hydrate plugs.

BACKGROUND

Natural gas hydrates are ice-like solids that form when methane gas and water are exposed to high pressures and low temperatures. Hydrates are formed when hydrogen-bonded water molecules organize into networks that can vary in size depending on the structure of the encapsulated guest molecules. Gas hydrates can be easily formed during the transportation of oil and gas in pipelines when the appropriate conditions are present. If hydrates are not managed properly, they often result in lost oil production, pipeline damage, and safety hazards to field workers.

There are several methods to avoid hydrate blockages. These methods include raising the temperature (e.g., insulation, and electric or water heating), lowering the pressure, removing the water, and adding anti-freeze chemicals. These techniques are often very expensive and difficult to manage. Perhaps the most common method of hydrate inhibition in the oil and gas industry is the addition of thermodynamic inhibitors (anti-freeze chemicals). These substances shift the hydrate formation temperature and therefore reduce the temperature at which the hydrates form at a given pressure and water content. Methanol and ethylene glycol are among the most common thermodynamic inhibitors used in the oil industry. Although thermodynamic inhibitors are quite effective, large doses are required to achieve high concentration in the water phase. Thermodynamic inhibitors are regularly dosed at concentrations as high as 50% based on water content during oil and gas production. Therefore, there is a substantial cost associated with the transportation and storage of large quantities of these solvents.

A more cost-effective alternative is the use of low dosage hydrate inhibitors (LDHIs); as they generally require less that 2% dose to inhibit the nucleation, growth, or agglomeration of gas hydrates. There are two general types of LDHIs, kinetic hydrate inhibitors (KHIs) and anti-agglomerants (AAs). KHIs work by delaying the growth of gas hydrate crystals and as anti-nucleators. AAs allow the hydrates to form, but they prevent them from agglomerating and accumulating into larger masses capable of causing plugs. An AA enables gas hydrates to form, but in the shape of fluid slurry dispersed in the liquid hydrocarbon phase. In general, the water cut should be below 50% otherwise the slurry becomes too viscous to transport. As consequence, significant research effort is being dedicated to develop AAs capable of operating under higher water-cuts, and there still exists a need for improved compounds, compositions and methods for preventing formation of gas hydrate agglomerates in the oil and gas industry.

SUMMARY

In one aspect, disclosed are beta-amino ester surfactant compounds having formula (I),

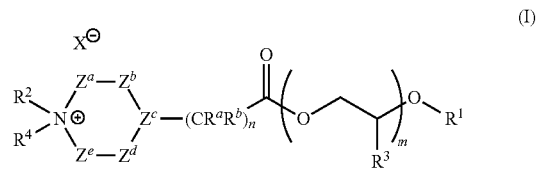

wherein
R$^1$ is alkyl, alkenyl, alkynyl, aryl, heteroaryl, cycloalkyl, or heterocyclyl;
R$^2$ is hydrogen, alkyl, alkenyl, alkynyl, cycloalkyl, or heterocyclyl, or R$^2$ may be absent;
R$^3$ is hydrogen or alkyl;
R$^4$ is alkyl, alkenyl, alkynyl, aryl, heteroaryl, cycloalkyl, or heterocyclyl;
Z$^a$ is C(R$^5$R$^6$), O, S, or N(R$^7$);
Z$^b$ is C(R$^8$R$^9$), O, S, or)N(R$^{10}$);
Z$^c$ is C(R$^{11}$) or N;
Z$^d$ is C(R$^{12}$R$^{13}$), O, S, or N(R$^{14}$);
Z$^e$ is C(R$^{15}$R$^{16}$), O, S, or N(R$^{17}$);
R$^5$, R$^6$, R$^7$, R$^8$, R$^9$, R$^{10}$, R$^{11}$, R$^{12}$, R$^{13}$, R$^{14}$, R$^{15}$, R$^{16}$, and R$^{17}$ are each independently selected from the group consisting of hydrogen, alkyl, alkenyl, alkynyl, aryl, heteroaryl, cycloalkyl, and heterocyclyl;
R$^a$ is independently selected from, at each occurrence, the group consisting of hydrogen, alkyl, alkenyl, alkynyl, aryl, heteroaryl, cycloalkyl, and heterocyclyl;
R$^b$ is independently selected from, at each occurrence, the group consisting of hydrogen, alkyl, alkenyl, alkynyl, aryl, heteroaryl, cycloalkyl, and heterocyclyl;
X$^-$ is a counterion or X$^-$ may be absent, provided that X$^-$ is present when R$^2$ is present and X$^-$ is absent when R$^2$ is absent;
m is any one of an integer from 1 to 100; and
n is any one of an integer from 1 to 50;
wherein said alkyl, alkenyl, alkynyl, aryl, heteroaryl, cycloalkyl, and heterocyclyl are each independently, at each occurrence, substituted or unsubstituted with a suitable substituent.

In certain embodiments, R$^1$ is unsubstituted C$_1$-C$_{22}$ alkyl or unsubstituted C$_2$-C$_{22}$ alkenyl; R$^2$ is absent; R$^3$ is hydrogen or unsubstituted C$_1$-C$_6$ alkyl; R$^4$ is unsubstituted C$_1$-C$_6$ alkyl; Z$^a$ is C(R$^5$R$^6$); Z$^b$ is C(R$^8$R$^9$); Z$^c$ is N; Z$^d$ is C(R$^{12}$R$^{13}$); Z$^e$ is C(R$^{15}$R$^{16}$), R$^5$, R$^6$, R$^8$, R$^9$, R$^{12}$, R$^{13}$, R$^{15}$, and R$^{16}$ are each independently selected from the group consisting of hydrogen and unsubstituted C$_1$-C$_6$ alkyl; R$^a$ is hydrogen at each occurrence; R$^b$ is hydrogen at each occurrence; X$^-$ is absent; m is any one of an integer from 1 to 20; and n is 2.

In certain embodiments, R$^1$ is unsubstituted C$_1$-C$_{22}$ alkyl or unsubstituted C$_2$-C$_{22}$ alkenyl; R$^2$ is unsubstituted C$_1$-C$_{10}$ alkyl; R$^3$ is hydrogen or unsubstituted C$_1$-C$_6$ alkyl; R$^4$ is unsubstituted C$_1$-C$_6$ alkyl; Z$^a$ is C(R$^5$R$^6$); Z$^b$ is C(R$^8$R$^9$); Z$^c$ is N; Z$^d$ is C(R$^{12}$R$^{13}$); Z$^e$ is C(R$^{15}$R$^{16}$), R$^5$, R$^6$, R$^8$, R$^9$, R$^{12}$, R$^{13}$, R$^{15}$, and R$^{16}$ are each independently selected from the group consisting of hydrogen and unsubstituted C$_1$-C$_6$ alkyl; R$^a$ is hydrogen at each occurrence; R$^b$ is hydrogen at each occurrence; X⁻ is bromide or chloride; m is any one of an integer from 1 to 20; and n is 2.

In certain embodiments, $R^3$ is hydrogen.

In certain embodiments, $R^5, R^6, R^8, R^9, R^{12}, R^{13}, R^{15}$, and $R^{16}$ are each independently hydrogen.

In certain embodiments, m is 2, 4, 10, or 20.

In certain embodiments, $R^1$ is —$C_{12}H_{25}$, —$C_{18}H_{37}$, or —$C_{18}H_{35}$.

In certain embodiments, the compound of formula (I) has formula (V),

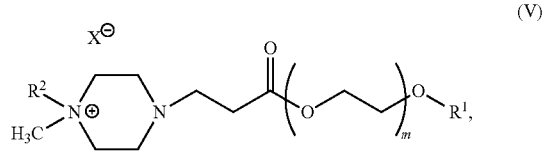

(V)

wherein $R^1$, $R^2$, $X^-$, and m are as defined above.

In certain embodiments, $R^1$ is —$(CH_2)_{11}CH_3$, —$(CH_2)_{17}CH_3$, or —$(CH_2)_8CH=CH(CH_2)_7CH_3$; $R^2$ is —$(CH_2)_3CH_3$, —$(CH_2)_5CH_3$, or $R^2$ is absent; and $X^-$ is bromide, or $X^-$ is absent, provided that $X^-$ is present when $R^2$ is present and $X^-$ is absent when $R^2$ is absent. In certain embodiments, m is 2, 4, 10, or 20.

In certain embodiments, the compound of formula (I) is selected from the group consisting of:

3,6,9,12-tetraoxatetracosyl 3-(4-methylpiperazin-1-yl)propanoate;

1-butyl-1-methyl-4-(3-oxo-4,7,10,13,16-pentaoxaoctacosyl)piperazin-1-ium bromide;

1-hexyl-1-methyl-4-(3-oxo-4,7,10,13,16-pentaoxaoctacosyl)piperazin-1-ium bromide;

(Z)-2-(2-(octadec-9-enyloxy)ethoxy)ethyl 3-(4-methylpiperazin-1-yl)propanoate;

(Z)-1-butyl-1-methyl-4-(3-(2-(2-(octadec-9-enyloxy)ethoxy)ethoxy)-3-oxopropyl)piperazin-1-ium bromide;

(Z)-1-hexyl-1-methyl-4-(3-(2-(2-(octadec-9-enyloxy)ethoxy)ethoxy)-3-oxopropyl)piperazin-1-ium bromide;

3,6,9,12,15,18,21,24,27,30-decaoxaoctatetracontyl 3-(4-methylpiperazin-1-yl)propanoate;

1-butyl-1-methyl-4-(3-oxo-4,7,10,13,16,19,22,25,28,31,34-undecaoxadopentacontyl)piperazin-1-ium bromide;

1-hexyl-1-methyl-4-(3-oxo-4,7,10,13,16,19,22,25,28,31,34-undecaoxadopentacontyl)piperazin-1-ium bromide;

3,6,9,12,15,18,21,24,27,30,33,36,39,42,45,48,51,54,57,60-icosaoxaoctaheptacontyl 3-(4-methylpiperazin-1-yl)propanoate;

1-butyl-1-methyl-4-(3-oxo-4,7,10,13,16,19,22,25,28,31,34,37,40,43,46,49,52,55,58,61,64-henicosaoxadooctacontyl)piperazin-1-ium bromide;

1-hexyl-1-methyl-4-(3-oxo-4,7,10,13,16,19,22,25,28,31,34,37,40,43,46,49,52,55,58,61,64-henicosaoxadooctacontyl)piperazin-1-ium bromide;

(Z)-3,6,9,12,15,18,21,24,27,30-decaoxaoctatetracont-39-enyl 3-(4-methylpiperazin-1-yl)propanoate;

(Z)-1-butyl-1-methyl-4-(3-oxo-4,7,10,13,16,19,22,25,28,31,34-undecaoxadopentacont-43-enyl)piperazin-1-ium bromide;

(Z)-1-hexyl-1-methyl-4-(3-oxo-4,7,10,13,16,19,22,25,28,31,34-undecaoxadopentacont-43-enyl)piperazin-1-ium bromide;

(Z)-3,6,9,12,15,18,21,24,27,30,33,36,39,42,45,48,51,54,57,60-icosaoxaoctaheptacont-69-enyl 3 -(4-methylpiperazin-1-yl)propanoate;

(Z)-1-butyl-1-methyl-4-(3-oxo-4,7,10,13,16,19,22,25,28,31,34,37,40,43,46,49,52,55,58,61,64-henicosaoxadooctacont-73-enyl)piperazin-1-ium bromide; and (Z)-1-hexyl-1-methyl-4-(3-oxo-4,7,10,13,16,19,22,25,28,31,34,37,40,43,46,49,52,55,58,61,64-henicosaoxadooctacont-73-enyl)piperazin-1-ium bromide.

In another aspect, disclosed are gas hydrate inhibitor compositions. In certain embodiments, the composition comprises one or more compounds of formula (I). In certain embodiments, the composition comprises a mixture of compounds of formula (I).

In certain embodiments, the composition comprises one or more additives independently selected from the group consisting of synergistic compounds, asphaltene inhibitors, paraffin inhibitors, corrosion inhibitors, scale inhibitors, emulsifiers, water clarifiers, dispersants, emulsion breakers, hydrogen sulfide scavengers, gas hydrate inhibitors, biocides, pH modifiers, surfactants, and solvents.

In certain embodiments, the composition comprises at least one solvent. In certain embodiments, the solvent is isopropanol, methanol, ethanol, heavy aromatic naptha, toluene, ethylene glycol, ethylene glycol monobutyl ether (EGMBE), diethylene glycol monoethyl ether, xylene, kerosene, diesel, isobutanol, heptane, or a combination thereof.

In another aspect, disclosed are methods of inhibiting the formation of hydrate agglomerates in a fluid or gas, the methods comprising adding to the fluid or gas an effective amount of a compound of formula (I). The fluid may comprise water, gas, and optionally liquid hydrocarbon. In certain embodiments, the fluid has a salinity of 1 to 20 w/w percent total dissolved solids (TDS). In certain embodiments, the fluid has a water cut from 1 to 65 v/v percent.

In certain embodiments, the method includes treating the fluid or gas with an effective amount of a composition comprising one or more compounds of formula (I). In certain embodiments, the composition further comprises one or more additional components, each component independently selected from the group consisting of synergistic compounds, asphaltene inhibitors, paraffin inhibitors, corrosion inhibitors, scale inhibitors, emulsifiers, water clarifiers, dispersants, emulsion breakers, hydrogen sulfide scavengers, gas hydrate inhibitors, biocides, pH modifiers, surfactants, and solvents. In certain embodiments, the composition comprises at least one solvent. In certain embodiments, the solvent is isopropanol, methanol, ethanol, heavy aromatic naptha, toluene, ethylene glycol, ethylene glycol monobutyl ether (EGMBE), diethylene glycol monoethyl ether, xylene, kerosene, diesel, isobutanol, heptane, or a combination thereof, or a combination thereof.

In certain embodiments, the method includes applying a compound of formula (I), or composition comprising a compound of formula (I), to a gas or liquid produced or used in the production, transportation, storage, and/or separation of crude oil and natural gas. In certain embodiments, the fluid or gas is contained in an oil or gas pipeline.

The compounds, compositions, methods and processes are further described herein.

DETAILED DESCRIPTION

Disclosed herein are beta-amino ester surfactant compounds and compositions, methods of using said compounds and compositions, and processes for their preparation. The compounds and compositions are particularly useful for the inhibition of gas hydrate agglomerates in crude oil and natural gas based products and processes. It is believed the surfactants disclosed herein present an optimal combination of hydrophilic portions (e.g., substituted piperazine) and hydrophobic portions (e.g., ethoxylated fatty alkyl groups), that together provide superior anti-agglomerate performance over available surfactants. The compounds and compositions can effectively inhibit the formation of gas hydrate plugs in crude oil and natural gas based products and processes.

1. Definition of Terms

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

The term "suitable substituent", as used herein, is intended to mean a chemically acceptable functional group, preferably a moiety that does not negate the activity of the inventive compounds. Such suitable substituents include, but are not limited to halo groups, perfluoroalkyl groups, perfluoroalkoxy groups, alkyl groups, alkenyl groups, alkynyl groups, hydroxy groups, oxo groups, mercapto groups, alkylthio groups, alkoxy groups, aryl or heteroaryl groups, aryloxy or heteroaryloxy groups, aralkyl or heteroaralkyl groups, aralkoxy or heteroaralkoxy groups, HO—(C=O)— groups, heterocylic groups, cycloalkyl groups, amino groups, alkyl- and dialkylamino groups, carbamoyl groups, alkylcarbonyl groups, alkoxycarbonyl groups, alkylaminocarbonyl groups, dialkylamino carbonyl groups, arylcarbonyl groups, aryloxycarbonyl groups, alkylsulfonyl groups, arylsulfonyl groups and the like. Those skilled in the art will appreciate that many substituents can be substituted by additional substituents.

The term "alkyl", as used herein, refers to a linear or branched hydrocarbon radical, preferably having 1, 2, 3, 4, 5, 6, 7, 8, 9, 10, 11, 12, 13, 14, 15, 16, 17, 18, 19, 20, 21, 22, 23, 24, 25, 26, 27, 28, 39, 30, 31, or 32 carbons. Alkyl groups include, but are not limited to, methyl, ethyl, n-propyl, isopropyl, n-butyl, iso-butyl, secondary-butyl, and tertiary-butyl. Alkyl groups may be unsubstituted or substituted by one or more suitable substituents, as defined above.

The term "alkylenyl" or "alkylene" as used herein, refers to a divalent group derived from a saturated, straight or branched hydrocarbon chain of from 1 to 32 carbon atoms. The term "$C_1$-$C_6$ alkylene" means those alkylene or alkylenyl groups having from 1 to 6 carbon atoms. Representative examples of alkylenyl groups include, but are not limited to, —$CH_2$—, —$CH(CH_3)$—, —$CH(C_2H_5)$—, —$CH(CH(CH_3)(C_2H_5))$—, —$C(H)(CH_3)CH_2CH_2$—, —$C(CH_3)_2$—, —$CH_2CH_2$—, —$CH_2CH_2CH_2$—, —$CH_2CH_2CH_2CH_2$—, and —$CH_2CH(CH_3)CH_2$—. Alkylenyl groups may be unsubstituted or substituted by one or more suitable substituents, as defined above.

The term "alkenyl", as used herein, refers to a straight or branched hydrocarbon radical, preferably having 2, 3, 4, 5, 6, 7, 8, 9, 10, 11, 12, 13, 14, 15, 16, 17, 18, 19, 20, 21, 22, 23, 24, 25, 26, 27, 28, 39, 30, 31, or 32 carbons, and having one or more carbon-carbon double bonds. Alkenyl groups include, but are not limited to, ethenyl, 1-propenyl, 2-propenyl (allyl), iso-propenyl, 2-methyl-1-propenyl, 1-butenyl, and 2-butenyl. Alkenyl groups may be unsubstituted or substituted by one or more suitable substituents, as defined above.

The term "alkenylenyl" or "alkenylene", as used herein, refers to a divalent group derived from a straight or branched chain hydrocarbon of 2 to 32 carbon atoms, which contains at least one carbon-carbon double bond. Representative examples of alkenylenyl groups include, but are not limited to, —$C(H)=C(H)$—, —$C(H)=C(H)$—$CH_2$—, —$C(H)=C(H)$—$CH_2$—$CH_2$—, —$CH_2$—$C(H)=C(H)$—$CH_2$—, —$C(H)=C(H)$—$CH(CH_3)$—, and —$CH_2$—$C(H)=C(H)$—$CH(CH_2CH_3)$—. Alkenylenyl groups may be unsubstituted or substituted by one or more suitable substituents, as defined above.

The term "alkynyl", as used herein, refers to a straight or branched hydrocarbon radical, preferably having 2, 3, 4, 5, 6, 7, 8, 9, 10, 11, 12, 13, 14, 15, 16, 17, 18, 19, 20, 21, 22, 23, 24, 25, 26, 27, 28, 39, 30, 31, or 32 carbons, and having one or more carbon-carbon triple bonds. Alkynyl groups include, but are not limited to, ethynyl, propynyl, and butynyl. Alkynyl groups may be unsubstituted or substituted by one or more suitable substituents, as defined above.

The term "alkynylenyl" or "alkynylene", as used herein, refers to a divalent unsaturated hydrocarbon group which may be linear or branched and which has at least one carbon-carbon triple bond. Representative examples of alkynylenyl groups include, but are not limited to, —C≡C—, —C≡C—$CH_2$—, —C≡C—$CH_2$—$CH_2$—, —$CH_2$—C≡C—$CH_2$—, —C≡C—$CH(CH_3)$—, and —$CH_2$—C≡C—$CH(CH_2CH_3)$—. Alkynylenyl groups may be unsubstituted or substituted by one or more suitable substituents, as defined above.

The term "alkoxy", as used herein, refers to an alkyl group, as defined herein, appended to the parent molecular moiety through an oxygen atom.

The term "aryl", as used herein, means monocyclic, bicyclic, or tricyclic aromatic radicals such as phenyl, naphthyl, tetrahydronaphthyl, indanyl and the like; optionally substituted by one or more suitable substituents, preferably 1 to 5 suitable substituents, as defined above.

The term "carbonyl", "(C=O)", or "—C(O)—" (as used in phrases such as alkylcarbonyl, alkyl —(C=O)— or alkoxycarbonyl) refers to the joinder of the >C=O moiety to a second moiety such as an alkyl or amino group (i.e. an amido group). Alkoxycarbonylamino (i.e. alkoxy(C=O)—NH—) refers to an alkyl carbamate group. The carbonyl group is also equivalently defined herein as (C=O). Alkylcarbonylamino refers to groups such as acetamide.

The term "cycloalkyl", as used herein, refers to a mono, bicyclic or tricyclic carbocyclic radical (e.g., cyclopropyl, cyclobutyl, cyclopentyl, cyclohexyl, cycloheptyl, cyclooctyl, cyclononyl, cyclopentenyl, cyclohexenyl, bicyclo[2.2.1]heptanyl, bicyclo[3.2.1]octanyl and bicyclo[5.2.0]nonanyl, etc.); optionally containing 1 or 2 double bonds. Cycloalkyl groups may be unsubstituted or substituted by one or more suitable substituents, preferably 1 to 5 suitable substituents, as defined above.

The term "halo" or "halogen", as used herein, refers to a fluoro, chloro, bromo or iodo radical.

The term "heteroaryl", as used herein, refers to a monocyclic, bicyclic, or tricyclic aromatic heterocyclic group containing one or more heteroatoms selected from O, S and N in the ring(s). Heteroaryl groups include, but are not limited to, pyridyl, pyrazinyl, pyrimidinyl, pyridazinyl, thienyl, furyl, imidazolyl, pyrrolyl, oxazolyl (e.g., 1,3-oxazolyl, 1,2-oxazolyl), thiazolyl (e.g., 1,2-thiazolyl, 1,3-thiazolyl), pyrazolyl, tetrazolyl, triazolyl (e.g., 1,2,3-triazolyl, 1,2,4-triazolyl), oxadiazolyl (e.g., 1,2,3-oxadiazolyl), thiadiazolyl (e.g., 1,3,4-thiadiazolyl), quinolyl, isoquinolyl, benzothienyl, benzofuryl, and indolyl. Heteroaryl groups may be unsubstituted or substituted by one or more suitable substituents, preferably 1 to 5 suitable substituents, as defined above.

The term "heterocycle" or "heterocyclyl", as used herein, refers to a monocyclic, bicyclic, or tricyclic group containing 1 to 4 heteroatoms selected from N, O, S(O)$_n$, NH or NR$^x$, wherein R$^x$ is a suitable substituent. Heterocyclic groups optionally contain 1 or 2 double bonds. Heterocyclic groups include, but are not limited to, azetidinyl, tetrahydrofuranyl, imidazolidinyl, pyrrolidinyl, piperidinyl, piperazinyl, oxazolidinyl, thiazolidinyl, pyrazolidinyl, thiomorpholinyl, tetrahydrothiazinyl, tetrahydro-thiadiazinyl, morpholinyl, oxetanyl, tetrahydrodiazinyl, oxazinyl, oxathiazinyl, indolinyl, isoindolinyl, quinuclidinyl, chromanyl, isochromanyl, and benzoxazinyl. Examples of monocyclic saturated or partially saturated ring systems are tetrahydrofuran-2-yl, tetrahydrofuran-3-yl, imidazolidin-1-yl, imidazolidin-2-yl, imidazolidin-4-yl, pyrrolidin-1-yl, pyrrolidin-2-yl, pyrrolidin-3-yl, piperidin-1-yl, piperidin-2-yl, piperidin-3-yl, piperazin-1-yl, piperazin-2-yl, piperazin-3-yl, 1,3-oxazolidin-3-yl, isothiazolidine, 1,3-thiazolidin-3-yl, 1,2-pyrazolidin-2-yl, 1,3-pyrazolidin-1-yl, thiomorpholin-yl, 1,2-tetrahydrothiazin-2-yl, 1,3-tetrahydrothiazin-3-yl, tetrahydrothiadiazin-yl, morpholin-yl, 1,2-tetrahydrodiazin-2-yl, 1,3-tetrahydrodiazin-1-yl, 1,4-oxazin-2-yl, and 1,2,5-oxathiazin-4-yl. Heterocyclic groups may be unsubstituted or substituted by one or more suitable substituents, preferably 1 to 3 suitable substituents, as defined above.

The term "hydroxy", as used herein, refers to an —OH group.

The term "oxo", as used herein, refers to a double bonded oxygen (═O) radical wherein the bond partner is a carbon atom. Such a radical can also be thought as a carbonyl group.

The term "cocoamine", as used herein, may refer to a mixture of amines comprising about 95% primary amines, and about 5% combined secondary and tertiary amines. The primary amines are about 6% hexylamine ($C_6$), about 7% decylamine ($C_{10}$), about 51% dodecylamine ($C_{12}$), about 19% tetradecylamine ($C_{14}$), about 9% hexadecylamine ($C_{16}$), about 2% octadecylamine ($C_{18}$), and about 6% combined content of octadecenylamine ($C_{18}$) and octadecadienylamine ($C_{18}$). The major component of cocoamine is $C_{12}H_{25}NH_2$. Cocoamine is sold under the product name ARMEEN® C by Akzo Nobel Surface Chemistry, LLC, 15200 Almeda Road, Houston, Tex. 77053, United States of America.

The term "coco", as used herein, may refes to a mixture of carbon chain radicals derived from cocoamine. The mixture of carbon chain radicals is about 6% hexyl ($C_6$), about 7% decyl ($C_{10}$), about 51% dodecyl ($C_{12}$), about 19% tetradecyl ($C_{14}$), about 9% hexadecyl ($C_{16}$), about 2% octadecyl ($C_{18}$), and about 6% combined content of octadecenyl ($C_{18}$) and octadecadienyl ($C_{18}$). The major component of coco is a —$C_{12}H_{25}$ carbon chain radical.

The term "counterion", as used herein, means a halide (e.g., fluoride, chloride, bromide, iodide), a carboxylate anion, such as selected from deprotonation of mineral acid, acrylic acid, acetic acid, methacrylic acid, glycolic acid, thioglycolic acid, propionic acid, butyric acid, and the like, or any other suitable anionic species.

The term "water cut", as used herein, means the percentage of water in a composition containing an oil and water mixture.

2. Compounds

Compounds of the invention include beta-amino ester surfactant compounds. The compounds may be particularly useful in the oil and gas industry for the inhibition of gas hydrate agglomerates.

In one aspect, compounds of the invention have formula (I),

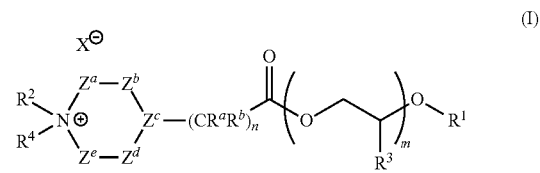

wherein

R$^1$ is alkyl, alkenyl, alkynyl, aryl, heteroaryl, cycloalkyl, or heterocyclyl;

R$^2$ is hydrogen, alkyl, alkenyl, alkynyl, cycloalkyl, or heterocyclyl, or R$^2$ may be absent;

R$^3$ is hydrogen or alkyl;

R$^4$ is alkyl, alkenyl, alkynyl, aryl, heteroaryl, cycloalkyl, or heterocyclyl;

Z$^a$ is C(R$^5$R$^6$), O, S, or N(R$^7$);

Z$^b$ is C(R$^8$R$^9$), O, S, or N(R$^{19}$);

Z$^c$ is C(R$^{11}$) or N;

Z$^d$ is C(R$^{12}$R$^{13}$), O, S, or N(R$^{14}$);

Z$^e$ is C(R$^{15}$R$^{16}$), O, S, or N(R$^{17}$);

R$^5$, R$^6$, R$^7$, R$^8$, R$^9$, R$^{10}$, R$^{11}$, R$^{12}$, R$^{13}$, R$^{14}$, R$^{15}$, R$^{16}$, and R$^{17}$ are each independently selected from the group consisting of hydrogen, alkyl, alkenyl, alkynyl, aryl, heteroaryl, cycloalkyl, and heterocyclyl;

R$^a$ is independently selected from, at each occurrence, the group consisting of hydrogen, alkyl, alkenyl, alkynyl, aryl, heteroaryl, cycloalkyl, and heterocyclyl;

R$^b$ is independently selected from, at each occurrence, the group consisting of hydrogen, alkyl, alkenyl, alkynyl, aryl, heteroaryl, cycloalkyl, and heterocyclyl;

X$^-$ is a counterion or X$^-$ may be absent, provided that X$^-$ is present when R$^2$ is present and X$^-$ is absent when R$^2$ is absent;

m is any one of an integer from 1 to 100; and n is any one of an integer from 1 to 50;

wherein said alkyl, alkenyl, alkynyl, aryl, heteroaryl, cycloalkyl, and heterocyclyl are each independently, at each occurrence, substituted or unsubstituted with a suitable substituent.

It is to be understood that when R$^2$ is absent, the corresponding nitrogen atom in the heterocyclic ring of formula (I) lacks the depicted positive charge.

In certain embodiments, R$^1$ is substituted or unsubstituted alkyl. In certain embodiments, R$^1$ is substituted or unsubstituted straight chain alkyl. In certain embodiments, R$^1$ is substituted or unsubstituted branched alkyl. In certain embodiments, R$^1$ is substituted or unsubstituted $C_1$-$C_{32}$ alkyl, substituted or unsubstituted $C_1$-$C_{22}$ alkyl, substituted or unsubstituted $C_1$-$C_{16}$ alkyl, substituted or unsubstituted $C_1$-$C_{10}$ alkyl, or substituted or unsubstituted $C_1$-$C_6$ alkyl. In certain embodiments, $R^1$ is substituted or unsubstituted straight chain $C_1$-$C_{22}$ alkyl. In certain embodiments, $R^1$ is substituted or unsubstituted branched $C_1$-$C_{22}$ alkyl.

In certain embodiments, $R^1$ is —$CH_3$, —$C_2H_5$, —$C_3H_7$, —$C_4H_9$, —$C_5H_{11}$, —$C_6H_{13}$, —$C_7H_{15}$, —$C_8H_{17}$, —$C_9H_{19}$, —$C_{10}H_{21}$, —$C_{11}H_{23}$, —$C_{12}H_{25}$, —$C_{13}H_{27}$, —$C_{14}H_{29}$, —$C_{15}H_{31}$, —$C_{16}H_{33}$, —$C_{17}H_{35}$, —$C_{18}H_{37}$, —$C_{19}H_{39}$, —$C_{20}H_{41}$, —$C_{21}H_{43}$, —$C_{22}H_{45}$, —$C_{23}H_{47}$, —$C_{24}H_{49}$, —$C_{25}H_{51}$, —$C_{26}H_{53}$, —$C_{27}H_{55}$, —$C_{28}H_{57}$, —$C_{29}H_{59}$, —$C_{30}H_{61}$, —$C_{31}H_{63}$, or —$C_{32}H_{65}$. In certain embodiments, $R^1$ is —$C_{12}H_{25}$. In certain embodiments, $R^1$ is —$C_{18}H_{37}$.

In certain embodiments, $R^1$ is —$CH_3$, —$CH_2CH_3$, —$(CH_2)_2CH_3$, —$(CH_2)_3CH_3$, —$(CH_2)_4CH_3$, —$(CH_2)_5CH_3$, —$(CH_2)_6CH_3$, —$(CH_2)_7CH_3$, —$(CH_2)_8CH_3$, —$(CH_2)_9CH_3$, —$(CH_2)_{10}CH_3$, —$(CH_2)_{11}CH_3$, —$(CH_2)_{12}CH_3$, —$(CH_2)_{13}CH_3$, —$(CH_2)_{14}CH_3$, —$(CH_2)_{15}CH_3$, —$(CH_2)_{16}CH_3$, —$(CH_2)_{17}CH_3$, —$(CH_2)_{18}CH_3$, —$(CH_2)_{19}CH_3$, —$(CH_2)_{20}CH_3$, —$(CH_2)_{21}CH_3$, —$(CH_2)_{22}CH_3$, —$(CH_2)_{23}CH_3$, —$(CH_2)_{24}CH_3$, —$(CH_2)_{25}CH_3$, —$(CH_2)_{26}CH_3$, —$(CH_2)_{27}CH_3$, —$(CH_2)_{28}CH_3$, —$(CH_2)_{29}CH_3$, —$(CH_2)_{30}CH_3$, —$(CH_2)_{31}CH_3$, or —$(CH_2)_{32}CH_3$. In certain embodiments, $R^1$ is —$(CH_2)_{11}CH_3$. In certain embodiments, $R^1$ is —$(CH_2)_{17}CH_3$.

In certain embodiments, $R^1$ is substituted or unsubstituted alkenyl. In certain embodiments, $R^1$ is substituted or unsubstituted straight chain alkenyl. In certain embodiments, $R^1$ is substituted or unsubstituted branched alkenyl. In certain embodiments, $R^1$ is substituted or unsubstituted $C_2$-$C_{32}$ alkenyl, substituted or unsubstituted $C_2$-$C_{22}$ alkenyl, substituted or unsubstituted $C_2$-$C_{16}$ alkenyl, substituted or unsubstituted $C_2$-$C_{10}$ alkenyl, or substituted or unsubstituted $C_2$-$C_6$ alkenyl. In certain embodiments, $R^1$ is substituted or unsubstituted $C_3$-$C_{32}$ alkenyl, substituted or unsubstituted $C_3$-$C_{22}$ alkenyl, substituted or unsubstituted $C_3$-$C_{16}$ alkenyl, or substituted or unsubstituted $C_{12}$-$C_{18}$ alkenyl. In certain embodiments, $R^1$ is substituted or unsubstituted straight chain $C_2$-$C_{22}$ alkenyl. In certain embodiments, is substituted or unsubstituted branched $C_2$-$C_{22}$ alkenyl.

In certain embodiments, $R^1$ is —$C_3H_5$, —$C_4H_7$, —$C_5H_9$, —$C_6H_{11}$, —$C_7H_{13}$, —$C_8H_{15}$, —$C_9H_{17}$, —$C_{10}H_{19}$, —$C_{11}H_{21}$, —$C_{12}H_{23}$, —$C_{13}H_{25}$, —$C_{14}H_{27}$, —$C_{15}H_{29}$, —$C_{16}H_{31}$, —$C_{17}H_{33}$, —$C_{18}H_{35}$, —$C_{19}H_{37}$, —$C_{20}H_{39}$, —$C_{21}H_{41}$, —$C_{22}H_{43}$, —$C_{23}H_{45}$, —$C_{24}H_{47}$, —$C_{25}H_{49}$, —$C_{26}H_{51}$, —$C_{27}H_{53}$, —$C_{28}H_{55}$, —$C_{29}H_{57}$, —$C_{30}H_{59}$, —$C_{31}H_{61}$, or —$C_{32}H_{63}$. In certain embodiments, $R^1$ is —$C_{18}H_{35}$.

In certain embodiments, $R^1$ is —$C_5H_7$, —$C_6H_9$, —$C_7H_{11}$, —$C_8H_{13}$, —$C_9H_{15}$, —$C_{10}H_{17}$, —$C_{11}H_{19}$, —$C_{12}H_{21}$, —$C_{13}H_{23}$, —$C_{14}H_{25}$, —$C_{15}H_{27}$, —$C_{16}H_{29}$, —$C_{17}H_{31}$, —$C_{18}H_{33}$, —$C_{19}H_{35}$, —$C_{20}H_{37}$, —$C_{21}H_{39}$, —$C_{22}H_{41}$, —$C_{23}H_{43}$, —$C_{24}H_{45}$, —$C_{25}H_{47}$, —$C_{26}H_{49}$, —$C_{27}H_{51}$, —$C_{28}H_{53}$, —$C_{29}H_{55}$, —$C_{30}H_{57}$, —$C_{31}H_{59}$, or —$C_{32}H_{61}$.

In certain embodiments, $R^1$ is —$C_7H_9$, —$C_8H_{11}$, —$C_9H_{13}$, —$C_{10}H_{15}$, —$C_{11}H_{17}$, —$C_{12}H_{19}$, —$C_{13}H_{21}$, —$C_{14}H_{23}$, —$C_{15}H_{25}$, —$C_{16}H_{27}$, —$C_{17}H_{29}$, —$C_{18}H_{31}$, —$C_{19}H_{33}$, —$C_{20}H_{35}$, —$C_{21}H_{37}$, —$C_{22}H_{39}$, —$C_{23}H_{41}$, —$C_{24}H_{43}$, —$C_{25}H_{45}$, —$C_{26}H_{47}$, —$C_{27}H_{49}$, —$C_{28}H_{51}$, —$C_{29}H_{53}$, —$C_{30}H_{55}$, —$C_{31}H_{57}$, or —$C_{32}H_{59}$.

In certain embodiments, $R^1$ is —$C_9H_{11}$, —$C_{10}H_{13}$, —$C_{11}H_{15}$, —$C_{12}H_{17}$, —$C_{13}H_{19}$, —$C_{14}H_{21}$, —$C_{15}H_{23}$, —$C_{16}H_{25}$, —$C_{17}H_{27}$, —$C_{18}H_{29}$, —$C_{19}H_{31}$, —$C_{20}H_{33}$, —$C_{21}H_{35}$, —$C_{22}H_{37}$, —$C_{23}H_{39}$, —$C_{24}H_{41}$, —$C_{25}H_{43}$, —$C_{26}H_{45}$, —$C_{27}H_{47}$, —$C_{28}H_{49}$, —$C_{29}H_{51}$, —$C_{30}H_{53}$, —$C_{31}H_{55}$, or —$C_{32}H_{57}$.

In certain embodiments, $R^1$ is —$C_{11}H_{13}$, —$C_{12}H_{15}$, —$C_{13}H_{17}$, —$C_{14}H_{19}$, —$C_{15}H_{21}$, —$C_{16}H_{23}$, —$C_{17}H_{25}$, —$C_{18}H_{27}$, —$C_{19}H_{29}$, —$C_{20}H_{31}$, —$C_{21}H_{33}$, —$C_{22}H_{35}$, —$C_{23}H_{37}$, —$C_{24}H_{39}$, —$C_{25}H_{41}$, —$C_{26}H_{43}$, —$C_{27}H_{45}$, —$C_{28}H_{47}$, —$C_{29}H_{49}$, —$C_{30}H_{51}$, —$C_{31}H_{53}$, or —$C_{32}H_{55}$.

In certain embodiments, $R^1$ is —$C_{13}H_{15}$, —$C_{14}H_{17}$, —$C_{15}H_{19}$, —$C_{16}H_{21}$, —$C_{17}H_{23}$, —$C_{18}H_{25}$, —$C_{19}H_{27}$, —$C_{20}H_{29}$, —$C_{21}H_{31}$, —$C_{22}H_{33}$, —$C_{23}H_{35}$, —$C_{24}H_{37}$, —$C_{25}H_{39}$, —$C_{26}H_{41}$, —$C_{27}H_{43}$, —$C_{28}H_{45}$, —$C_{29}H_{47}$, —$C_{30}H_{49}$, —$C_{31}H_{51}$, or —$C_{32}H_{53}$.

In certain embodiments, $R^1$ is —$(CH_2)_2CH$=$CHCH_2CH$=$CHCH_2CH$=$CHCH_2CH$=$CHCH_2CH$=$CH(CH_2)_4CH_3$, —$(CH_2)_2CH$=$CHCH_2CH$=$CHCH_2CH$=$CHCH_2CH$=$CHCH_2CH$=$CHCH_2CH$=$CHCH_2CH_3$, —$(CH_2)_3CH$=$CHCH_2CH$=$CHCH_2CH$=$CH(CH_2)_7CH_3$, —$(CH_2)_3CH$=$CHCH_2CH_2CH$=$CHCH_2CH$=$CH(CH_2)_4CH_3$, —$(CH_2)_3CH$=$CH(CH_2)_4CH$=$CHCH_2CH$=$CH(CH_2)_4CH_3$, —$(CH_2)_3CH$=$CHCH_2CH$=$CHCH_2CH$=$CHCH_2CH$=$CH(CH_2)_4CH_3$, —$(CH_2)_3CH$=$CHCH_2CH$=$CHCH_2CH$=$CHCH_2CH$=$CHCH_2CH$=$CHCH_2CH_3$, —$(CH_2)_3CH$=$CHCH$=$CHCH$=$CHCH$=$CHCH$=$CH(CH_2)_4CH_3$, —$(CH_2)_4CH$=$CH(CH_2)_8CH_3$, —$(CH_2)_4CH$=$CHCH_2CH$=$CHCH_2CH$=$CH(CH_2)_4CH_3$, —$(CH_2)_4CH$=$CHCH_2CH$=$CHCH_2CH$=$CHCH_2CH$=$CHCH_2CH_3$, —$(CH_2)_4CH$=$CHCH_2CH$=$CHCH_2CH$=$CHCH_2CH$=$CHCH_2CH$=$CHCH_2CH_3$, —$(CH_2)_4CH$=$CHCH_2CH$=$CHCH_2CH$=$CHCH_2CH$=$CHCH_2CH$=$CHCH_2CH$=$CH(CH_2)_4CH_3$, —$(CH_2)_4CH$=$CHCH_2CH$=$CHCH_2CH$=$CHCH_2CH$=$CHCH_2CH$=$CHCH_2$ $CH_3$, —$(CH_2)_5CH$=$CHCH_2CH$=$CHCH_2CH$=$CHCH_2CH$=$CHCH_2CH_3$, —$(CH_2)_5CH$=$CHCH_2CH$=$CHCH_2CH$=$CHCH_2CH$=$CH(CH_2)_4CH_3$, —$(CH_2)_5CH$=$CHCH_2CH$=$CHCH_2CH$=$CHCH_2CH$=$CHCH_2CH$=$CHCH_2CH_3$, —$(CH_2)_6CH$=$CHCH$=$CHCH$=$CH(CH_2)_4CH_3$, —$(CH_2)_6CH$=$CHCH_2CH$=$CHCH_2CH$=$CHCH_2CH$=$CH(CH_2)_4CH_3$, —$(CH_2)_7CH$=$CH(CH_2)_3CH_3$, —$(CH_2)_7CH$=$CH(CH_2)_5CH_3$, —$(CH_2)_7CH$=$CH(CH_2)_7CH_3$, —$(CH_2)_7CH$=$CHCH$=$CHCH$=$CH(CH_2)_3CH_3$, —$(CH_2)_7CH$=$CHCH$=$CH(CH_2)_5CH_3$, —$(CH_2)_7CH$=$CHCH_2CH$=$CH(CH_2)_4CH_3$, —$(CH_2)_7CH$=$CHCH_2CH$=$CH(CH_2)_4CH_3$, —$(CH_2)_7CH$=$CHCH$=$CHCH_2CH_2CH$=$CHCH_2CH_3$, —$(CH_2)_7CH$=$CHCH$=$CHCH$=$CHCH$=$CHCH_2CH_3$, —$(CH_2)_7CH$=$CHCH_2CH$=$CHCH_2CH$=$CHCH_2CH$=$CH(CH_2)_4CH_3$, —$(CH_2)_7CH$=$CHCH_2CH$=$CHCH_2CH$=$CHCH_2CH_3$, —$(CH_2)_7CH$=$CHCH_2CH$=$CHCH_2CH$=$CHCH_2CH$=$CHCH_2CH_3$, —$(CH_2)_8CH$=$CH(CH_2)_7CH_3$, —$(CH_2)_9CH$=$CH(CH_2)_5CH_3$, —$(CH_2)_9CH$=$CHCH_2CH$=$CH(CH_2)_4CH_3$, —$(CH_2)_9CH$=$CHCH_2CH$=$CHCH_2CH$=$CHCH_2CH_3$, —$(CH_2)_9CH$=$CH(CH_2)_7CH_3$, —$(CH_2)_{11}CH$=$CH(CH_2)_5CH_3$, —$(CH_2)_{11}CH$=$CH(CH_2)_7CH_3$, —$(CH_2)_{11}CH$=$CHCH_2CH$=$CH(CH_2)_4CH_3$, or —$(CH_2)_{13}CH$=$CH(CH_2)_7CH_3$.

In certain embodiments, $R^1$ is (Z)-tetradec-9-enyl, (Z)-hexadec-9-enyl, (Z)-hexadec-6-enyl, (Z)-octadec-9-enyl, (E)-octadec-9-enyl, (E)-octadec-11-enyl, (9Z,12Z)-octadeca-9,12-dienyl, (9E,12E)-octadeca-9,12-dienyl, (9Z,12Z,15Z)-octadeca-9,12,15-trienyl, (5Z,8Z,11Z,14Z)-icosa-5,8,11,14-tetraenyl, (5Z,8Z,11Z,14Z,17Z)-icosa-5,8,11,14,17-pentaenyl, (Z)-docos-13-enyl, (4Z,7Z,10Z,13Z,16Z,19Z)-docosa-4,7,10,13,16,19-hexaenyl, (7Z,10Z,13Z)-hexadeca-7,10,13-trienyl, (6Z,9Z,12Z,15Z)-octadeca-6,9,12,15-tetraenyl, (11Z,14Z,17Z)-icosa-11,14,17-trienyl, (5Z,8Z, 11Z,14Z,17Z)-icosa-5,8,11,14,17-pentaenyl, (6Z,9Z,12Z, 15Z,18Z)-henicosa-6,9,12,15,18-pentaenyl, (7Z,10Z,13Z, 16Z,19Z)-docosa-7,10,13,16,19-pentaenyl, (4Z,7Z,10Z, 13Z,16Z)-docosa-4,7,10,13,16-pentaenyl, (9Z,12Z,15Z, 18Z,21Z)-tetracosa-9,12,15,18,21-pentaenyl, (6Z,9Z,12Z, 15Z,18Z,21Z)-tetracosa-6,9,12,15,18,21-hexaenyl, (6Z,9Z, 12Z)-octadeca-6,9,12-trienyl, (11Z,14Z)-icosa-11,14-dienyl, (8Z,11Z,14Z)-icosa-8,11,14-trienyl, (13Z,16Z)-docosa-13,16-dienyl, (7Z,10Z,13Z,16Z)-docosa-7,10,13,16-tetraenyl, (9Z,12Z,15Z,18Z)-tetracosa-9,12,15,18-tetraenyl, (6Z,9Z,12Z,15Z,18Z)-tetracosa-6,9,12,15,18-pentaenyl, (Z)-eicos-11-enyl, (Z)-icos-13-enyl, (5Z,8Z, 11Z)-eicosa-5,8,11-trienyl, (Z)-tetracos-15-enyl, (9Z,11E)-octadeca-9,11-dienyl, (8E,10E,12Z)-octadeca-8,10,12-trienyl, (8E,10E,12E)-octadeca-8,10,12-trienyl, (8E,10Z, 12E)-octadeca-8,10,12-trienyl, (9Z,11E,13E)-octadeca-9, 11,13-trienyl, (9E,11E,13E)-octadeca-9,11,13-trienyl, (9E, 11E,13Z)-octadeca-9,11,13-trienyl, (9Z,11E,13Z)-octadeca-9,11,13-trienyl, (9E,11Z,15E)-octadeca-9,11,15-trienyl, (9Z,11E,13E,15Z)-octadeca-9,11,13,15-tetraenyl, (9E,11E, 13E,15E)-octadeca-9,11,13,15-tetraenyl, (5Z,8Z,10E,12E, 14Z)-icosa-5,8,10,12,14-pentaenyl, (5Z,9Z,12Z)-octadeca-5,9,12-trienyl, or (5Z,11Z,14Z)-icosa-5,11,14-trienyl. In certain embodiments, $R^1$ is (Z)-octadec-9-enyl.

In certain embodiments, $R^1$ is substituted or unsubstituted alkynyl. In certain embodiments, $R^1$ is substituted or unsubstituted straight chain alkynyl. In certain embodiments, $R^1$ is substituted or unsubstituted branched alkynyl. In certain embodiments, $R^1$ is substituted or unsubstituted $C_2$-$C_{32}$ alkynyl, substituted or unsubstituted $C_2$-$C_{22}$ alkynyl, substituted or unsubstituted $C_2$-$C_{16}$ alkynyl, substituted or unsubstituted $C_2$-$C_{10}$ alkynyl, or substituted or unsubstituted $C_2$-$C_6$ alkynyl. In certain embodiments, $R^1$ is substituted or unsubstituted straight chain $C_2$-$C_{22}$ alkynyl. In certain embodiments, $R^1$ is substituted or unsubstituted branched $C_2$-$C_{22}$ alkynyl.

In certain embodiments, $R^1$ is substituted or unsubstituted aryl. In certain embodiments, $R^1$ is substituted or unsubstituted phenyl. In certain embodiments, $R^1$ is 4-octylphenyl. In certain embodiments, $R^1$ is 4-nonylphenyl. In certain embodiments, $R^1$ is 2,4,6-tri-tertbutylphenyl.

In certain embodiments, $-(OCH_2CHR^3)_mOR^1$ of formula (I), and thus $R^1$, is derived from a fatty alcohol of formula: $HO(CH_2CHR^3O)_mR^1$, wherein $R^1$, $R^3$, and m are as defined herein. In certain embodiments, the fatty alcohol is an ethoxylated fatty alcohol or a propoxylated fatty alcohol. In certain embodiments, $-(OCH_2CHR^3)_mOR^1$ of formula (I) is derived from $HO(CH_2CH_2O)_4C_{12}H_{25}$ sold under the tradename Brij™ L4 by Sigma Aldrich, St. Louis, Mo. In certain embodiments, $-(OCH_2CHR^3)_mOR^1$ of formula (I) is derived from $HO(CH_2CH_2O)_{20}C_{16}H_{33}$ sold under the tradename Brij™ 58 by Sigma Aldrich. In certain embodiments, $-(OCH_2CHR^3)_mOR^1$ of formula (I) is derived from $HO(CH_2CH_2O)_mC_{18}H_{35}$, wherein m~20, sold under the tradename Brij™ 98 by Sigma Aldrich. In certain embodiments, $-(OCH_2CHR^3)_mOR^1$ of formula (I) is derived from $HO(CH_2CH_2O)_mC_{16}H_{33}$, wherein m~2, sold under the tradename Brij™ 52 by Sigma Aldrich. In certain embodiments, $-(OCH_2CHR^3)_mOR^1$ of formula (I) is derived from $HO(CH_2CH_2O)_mC_{18}H_{37}$, wherein m~100, sold under the tradename Brij™ S 100 by Sigma Aldrich. In certain embodiments, $-(OCH_2CHR^3)_mOR^1$ of formula (I) is derived from $HO(CH_2CH_2O)_{23}C_{12}H_{25}$, sold under the tradename Brij™ L23 by Sigma Aldrich. In certain embodiments, $-(OCH_2CHR^3)_mOR^1$ of formula (I) is derived from $HO(CH_2CH_2O)_mC_{18}H_{35}$, wherein m~2, sold under the tradename Brij™ 93 by Sigma Aldrich. In certain embodiments, $-(OCH_2CHR^3)_mOR^1$ of formula (I) is derived from $HO(CH_2CH_2O)_mC_{16}H_{33}$, wherein m~10, sold under the tradename Brij™ C10 by Sigma Aldrich. In certain embodiments, $-(OCH_2CHR^3)_mOR^1$ of formula (I) is derived from $HO(CH_2CH_2O)_mC_{18}H_{35}$, wherein m~10, sold under the tradename Brij™ C10 by Sigma Aldrich. In certain embodiments, $-(OCH_2CHR^3)_mOR^1$ of formula (I) is derived from $HO(CH_2CH_2O)_mC_{18}H_{37}$, wherein m~10, sold under the tradename Brij™ S10 by Sigma Aldrich. In certain embodiments, $-(OCH_2CHR^3)_mOR^1$ of formula (I) is derived from $HO(CH_2CH_2O)_mC_{18}H_{37}$, wherein m~20, sold under the tradename Brij™0 S20 by Sigma Aldrich. In certain embodiments, $-(OCH_2CHR^3)_mOR^1$ of formula (I) is derived from $HO(CH_2CH_2O)_2C_{18}H_{37}$, sold under the tradename Brij™ S2 by Sigma Aldrich.

In certain embodiments, $-(OCH_2CHR^3)_mOR^1$ of formula (I) is derived from $HO(CH_2CH(CH_3)O)_{10}C_{16}H_{33}$, sold under the tradename Procetyl™ 10 by Croda Chemicals Europe, East Yorkshire, England. In certain embodiments, $-(OCH_2CHR^3)_mOR^1$ of formula (I) is derived from $HO(CH_2CH(CH_3)O)_{15}C_{18}H_{37}$, sold under the tradename Prostearyl™ 15 by Croda Chemicals Europe.

In certain embodiments, $R^2$ is hydrogen.

In certain embodiments, $R^2$ is substituted or unsubstituted alkyl. In certain embodiments, $R^2$ is substituted or unsubstituted straight chain alkyl. In certain embodiments, $R^2$ is substituted or unsubstituted branched alkyl. In certain embodiments, $R^2$ is substituted or unsubstituted $C_1$-$C_{10}$ alkyl, or substituted or unsubstituted $C_1$-$C_6$ alkyl.

In certain embodiments, $R^2$ is $-CH_3$, $-C_2H_5$, $-C_3H_7$, $-C_4H_9$, $-C_5H_{11}$, $-C_6H_{13}$, $-C_7H_{15}$, $-C_8H_{17}$, $-C_9H_{19}$, or $-C_{10}H_{21}$. In certain embodiments, $R^2$ is $-C_4H_9$. In certain embodiments, $R^2$ is $-C_6H_{13}$. In certain embodiments, $R^2$ is $-CH_3$, $-CH_2CH_3$, $-(CH_2)_2CH_3$, $-(CH_2)_3CH_3$, $-(CH_2)_4CH_3$, $-(CH_2)_5CH_3$, $-(CH_2)_6CH_3$, $-(CH_2)_7CH_3$, $-(CH_2)_8CH_3$, or $-(CH_2)_9CH_3$. In certain embodiments, $R^2$ is $-(CH_2)_3CH_3$. In certain embodiments, $R^2$ is $-(CH_2)_5CH_3$.

In certain embodiments, $R^2$ is $-CH_2$-aryl, wherein aryl is substituted or unsubstituted. In certain embodiments, $R^2$ is unsubstituted benzyl (i.e., $-CH_2C_6H_5$).

In certain embodiments, $R^2$ is substituted or unsubstituted alkenyl. In certain embodiments, $R^2$ is substituted or unsubstituted straight chain alkenyl. In certain embodiments, $R^2$ is substituted or unsubstituted branched alkenyl. In certain embodiments, $R^2$ is substituted or unsubstituted $C_2$-$C_{10}$ alkenyl, or substituted or unsubstituted $C_2$-$C_6$ alkenyl. In certain embodiments, $R^2$ is substituted or unsubstituted $C_3$-$C_{10}$ alkenyl, or substituted or unsubstituted $C_3$-$C_6$ alkenyl.

In certain embodiments, $R^2$ is $-C_3H_5$, $-C_4H_7$, $-C_5H_9$, $-C_6H_{11}$, $-C_7H_{13}$, $-C_8H_{15}$, $-C_9H_{17}$, or $-C_{10}H_{19}$. In certain embodiments, $R^2$ is $-C_5H_7$, $-C_6H_9$, $-C_7H_{11}$, $-C_8H_{13}$, $-C_9H_{15}$, or $-C_{10}H_{17}$. In certain embodiments, $R^2$ is $-C_7H_9$, $-C_8H_{11}$, $-C_9H_{13}$, or $-C_{10}H_{15}$. In certain embodiments, $R^2$ is $-C_9H_{11}$, or $-C_{10}H_{13}$.

In certain embodiments, $R^2$ is substituted or unsubstituted alkynyl. In certain embodiments, $R^2$ is substituted or unsubstituted straight chain alkynyl. In certain embodiments, $R^2$ is substituted or unsubstituted branched alkynyl. In certain embodiments, $R^2$ is substituted or unsubstituted $C_2$—$C_{10}$ alkynyl, or substituted or unsubstituted $C_2$-$C_6$ alkynyl. In certain embodiments, $R^2$ is substituted or unsubstituted $C_3$-$C_{10}$ alkynyl, or substituted or unsubstituted $C_3$-$C_6$ alkynyl. In certain embodiments, $R^2$ is $-CH_2C{\equiv}CH$, $-CH_2C{\equiv}CCH_3$, $-CH_2C{\equiv}CCH_2CH_3$, $-CH_2CH_2C{\equiv}CH$, $-CH_2CH_2C{\equiv}CCH_3$, or $-CH_2CH_2C{\equiv}CCH_2CH_3$.

In certain embodiments, $R^2$ is absent.

In certain embodiments $R^3$ is hydrogen.

In certain embodiments, $R^3$ is substituted or unsubstituted alkyl. In certain embodiments, $R^3$ is substituted or unsubstituted straight chain alkyl. In certain embodiments, $R^3$ is substituted or unsubstituted branched alkyl. In certain embodiments, $R^3$ is substituted or unsubstituted $C_1$-$C_{10}$ alkyl, or substituted or unsubstituted $C_1$-$C_6$ alkyl.

In certain embodiments, $R^3$ is —$CH_3$, —$C_2H_5$, —$C_3H_7$, —$C_4H_9$, —$C_5H_{11}$, —$C_6H_{13}$, —$C_7H_{15}$, —$C_8H_{17}$, —$C_9H_{19}$, or —$C_{10}H_{21}$. In certain embodiments, $R^3$ is —$CH_3$, —$CH_2CH_3$, —$(CH_2)_2CH_3$, —$(CH_2)_3CH_3$, —$(CH_2)_4CH_3$, —$(CH_2)_5CH_3$, —$(CH_2)_6CH_3$, —$(CH_2)_7CH_3$, —$(CH_2)_8CH_3$, or —$(CH_2)_9CH_3$ In certain embodiments, $R^3$ is methyl (—$CH_3$).

In certain embodiments, $R^4$ is substituted or unsubstituted alkyl. In certain embodiments, $R^4$ is substituted or unsubstituted straight chain alkyl. In certain embodiments, $R^4$ is substituted or unsubstituted branched alkyl. In certain embodiments, $R^4$ is substituted or unsubstituted $C_1$-$C_{10}$ alkyl, or substituted or unsubstituted $C_1$-$C_6$ alkyl.

In certain embodiments, $R^4$ is —$CH_3$, —$C_2H_5$, —$C_3H_7$, —$C_4H_9$, —$C_5H_{11}$, —$C_6H_{13}$, —$C_7H_{15}$, —$C_8H_{17}$, —$C_9H_{19}$, or —$C_{10}H_{21}$. In certain embodiments, $R^4$ is —$CH_3$, —$CH_2CH_3$, —$(CH_2)_2CH_3$, —$(CH_2)_3CH_3$, —$(CH_2)_4CH_3$, —$(CH_2)_5CH_3$, —$(CH_2)_6CH_3$, —$(CH_2)_7CH_3$, —$(CH_2)_8CH_3$, or —$(CH_2)_9CH_3$ In certain embodiments, $R^4$ is methyl (—$CH_3$).

In certain embodiments, $R^4$ is substituted or unsubstituted alkenyl. In certain embodiments, $R^4$ is substituted or unsubstituted straight chain alkenyl. In certain embodiments, $R^4$ is substituted or unsubstituted branched alkenyl. In certain embodiments, $R^4$ is substituted or unsubstituted $C_2$-$C_{10}$ alkenyl, substituted or unsubstituted $C_2$-$C_6$ alkenyl, or substituted or unsubstituted $C_3$-$C_6$ alkenyl.

In certain embodiments, $R^4$ is —$C_3H_5$, —$C_4H_7$, —$C_5H_9$, —$C_6H_{11}$, —$C_7H_{13}$, —$C_8H_{15}$, —$C_9H_{17}$, or —$C_{10}H_{19}$. In certain embodiments, $R^4$ is —$C_5H_7$, —$C_6H_9$, —$C_7H_{11}$, —$C_8H_{13}$, —$C_9H_{15}$, or —$C_{10}H_{17}$. In certain embodiments, $R^4$ is —$C_7H_9$, —$C_8H_{11}$, —$C_9H_{13}$, or —$C_{10}H_{15}$. In certain embodiments, $R^4$ is —$C_9H_{11}$, or —$C_{10}H_{13}$.

In certain embodiments, $R^4$ is substituted or unsubstituted alkynyl. In certain embodiments, $R^4$ is substituted or unsubstituted straight chain alkynyl. In certain embodiments, $R^4$ is substituted or unsubstituted branched alkynyl. In certain embodiments, $R^4$ is substituted or unsubstituted $C_2$-$C_{10}$ alkynyl, substituted or unsubstituted $C_2$-$C_6$ alkynyl, or substituted or unsubstituted $C_3$-$C_6$ alkynyl. In certain embodiments, $R^4$ is —$CH_2C\equiv CH$, —$CH_2C\equiv CCH_3$, —$CH_2C\equiv CCH_2CH_3$, —$CH_2CH_2C\equiv CH$, —$CH_2CH_2C\equiv CCH_3$, or —$CH_2CH_2C\equiv CCH_2CH_3$.

In certain embodiments, $Z^a$ is $C(R^5R^6)$ or $N(R^7)$; $Z^b$ is $C(R^8R^9)$ or $N(R^{10})$; $Z^c$ is N; $Z^d$ is $C(R^{12}R^{13})$ or $N(R^{14})$; and $Z^e$ is $C(R^{15}R^{16})$ or $N(R^{17})$. In certain embodiments, $Z^a$ is $C(R^5R^6)$; $Z^b$ is $C(R^8R^9)$; $Z^c$ is N; $Z^d$ is $C(R^{12}R^{13})$; and $Z^e$ is $C(R^{15} R^{16})$. In certain embodiments, $Z^a$ is $C(R^5R^6)$; $Z^b$ is $C(R^8R^9)$; $Z^c$ is $C(R^{11})$, $Z^d$ is $C(R^{12}R^{13})$; and $Z^e$ is $C(R^{15}R^{16})$.

In certain embodiments, $Z^a$ is $C(R^5R^6)$, $Z^b$ is $C(R^8R^9)$; $Z^c$ is N; $Z^d$ is $C(R^{12}R^{13})$, $Z^e$ is $C(R^{15}R^{16})$, and $R^5$, $R^6$, $R^8$, $R^9$, $R^{12}$, $R^{13}$, $R^{15}$, and $R^{16}$ are each independently selected from the group consisting of hydrogen, $C_1$-$C_6$ alkyl, $C_2$-$C_6$ alkenyl, $C_2$-$C_6$ alkynyl, six-membered aryl, five- or six-membered heteroaryl, $C_3$-$C_8$ cycloalkyl, and five- or six-membered heterocyclyl. In certain embodiments, $Z^a$ is $C(R^5R^6)$, $Z^b$ is $C(R^8R^9)$; $Z^c$ is N; $Z^d$ is $C(R^{12}R^{13})$; $Z^e$ is $C(R^{15}R^{16})$; and $R^5$, $R^6$, $R^8$, $R^9$, $R^{12}$, $R^{13}$, $R^{15}$, and $R^{16}$ are each independently selected from the group consisting of hydrogen and $C_1$-$C_6$ alkyl. In certain embodiments, $Z^a$ is $C(R^5R^6)$, $Z^b$ is $C(R^8R^9)$; $Z^c$ is N; $Z^d$ is $C(R^{12}R^{13})$; $Z^e$ is $C(R^{15}R^{16})$; and $R^5$, $R^6$, $R^8$, $R^9$, $R^{12}$, $R^{13}$, $R^{15}$, and $R^{16}$ are each hydrogen.

In certain embodiments, $R^a$ and $R^b$ are each independently selected from, at each occurrence, the group consisting of hydrogen, $C_1$-$C_6$ alkyl, $C_2$-$C_6$ alkenyl, $C_2$-$C_6$ alkynyl, six-membered aryl, five- or six-membered heteroaryl, $C_3$-$C_8$ cycloalkyl, and five- or six-membered heterocyclyl. In certain embodiments, $R^a$ and $R^b$ are each independently selected from, at each occurrence, the group consisting of hydrogen and $C_1$-$C_6$ alkyl. In certain embodiments, $R^a$ and $R^b$ are each hydrogen.

In certain embodiments, $X^-$ is fluoride, chloride, bromide, iodide, or carboxylate anion, such as selected from deprotonation of mineral acid, acrylic acid, acetic acid, methacrylic acid, glycolic acid, thioglycolic acid, propionic acid, or butyric acid. In certain embodiments, $X^-$ is chloride or bromide. In certain embodiments, $X^-$ is bromide.

In certain embodiments, m is any one of an integer from 1 to 30 (i.e., m is 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30). In certain embodiments, m is any one of an integer from 1 to 20 (i.e., m is 1, 2, 3, 4, 5, 6, 7, 8, 9, 10, 11, 12, 13, 14, 15, 16, 17, 18, 19, or 20). In certain embodiments, m is 2, 4, 10, or 20. In certain embodiments, m is 2. In certain embodiments, m is 4. In certain embodiments, m is 10. In certain embodiments, m is 20.

In certain embodiments, n is any one of an integer from 1 to 30 (i.e., n is 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30). In certain embodiments, n is any one of an integer from 1 to 10 (i.e., n is 1, 2, 3, 4, 5, 6, 7, 8, 9, or 10). In certain embodiments, n is 2.

In another aspect, compounds of the invention have formula (II),

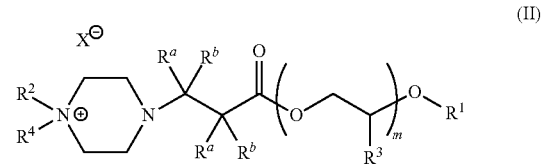

(II)

wherein $R^1$, $R^2$, $R^3$, $R^4$, $R^a$, $R^b$, $X^-$, and m are as defined above.

In one preferred embodiment, $R^1$ is alkyl, alkenyl, or alkynyl; $R^2$ is hydrogen, alkyl, or benzyl, or $R^2$ is absent; $R^3$ is alkyl or hydrogen; $R^4$ is alkyl; each $R^a$ is independently hydrogen or alkyl; each $R^b$ is independently hydrogen or alkyl; $X^-$ is a counterion or $X^-$ is absent; and m is any one of an integer from 1 to 20. In another preferred embodiment, $R^1$ is $C_1$-$C_{22}$ alkyl, or $C_1$-$C_{22}$ alkenyl; $R^2$ is $C_1$-$C_6$ alkyl, or $R^2$ is absent; $R^3$ is methyl or hydrogen; $R^4$ is $C_1$-$C_6$ alkyl; each $R^a$ is independently hydrogen or $C_1$-$C_6$ alkyl; each $R^b$ is independently hydrogen or $C_1$-$C_6$ alkyl; $X^-$ is bromide or chloride, or $X^-$ is absent; and m is any one of an integer from 1 to 20. In another preferred embodiment, $R^1$ is —$C_{12}H_{25}$, —$C_{18}H_{35}$, or —$C_{18}H_{37}$; $R^2$ is —$C_4H_9$ or —$C_6H_{13}$, or $R^2$ is absent; $R^3$ is H or —$CH_3$; $R^4$ is —$CH_3$; each $R^a$ is hydrogen; each $R^b$ is hydrogen; $X^-$ is bromide or $X^-$ is absent; and m is 2, 4, 10, or 20. It is to be understood that when $R^2$ is absent, then $X^-$ is absent; and when $R^2$ is present, $X^-$ is present. It is also to be understood that when $R^2$ is absent, the corresponding nitrogen atom in the piperazine ring of formula (II) lacks the depicted positive charge.

In another aspect, compounds of the invention have formula (III),

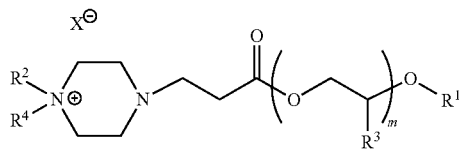

wherein $R^1$, $R^2$, $R^3$, $R^4$, $X^-$, and m are as defined above.

In one preferred embodiment, $R^1$ is alkyl, alkenyl, or alkynyl; $R^2$ is hydrogen, alkyl, or benzyl, or $R^2$ is absent; $R^3$ is alkyl or hydrogen; $R^4$ is alkyl; $X^-$ is a counterion or $X^-$ is absent; and m is any one of an integer from 1 to 20. In another preferred embodiment, $R^1$ is $C_1$-$C_{22}$ alkyl, or $C_1$-$C_{22}$ alkenyl; $R^2$ is $C_1$-$C_6$ alkyl, or $R^2$ is absent; $R^3$ is methyl or hydrogen; $R^4$ is $C_1$-$C_6$ alkyl; $X^-$ is bromide or chloride, or $X^-$ is absent; and m is any one of an integer from 1 to 20. In another preferred embodiment, $R^1$ is —$C_{12}H_{25}$, —$C_{18}H_{35}$, or —$C_{18}H_{37}$; $R^2$ is —$C_4H_9$ or —$C_6H_{13}$, or $R^2$ is absent; $R^3$ is H or —$CH_3$; $R^4$ is —$CH_3$; $X^-$ is bromide or $X^-$ is absent; and m is 2, 4, 10, or 20. It is to be understood that when $R^2$ is absent, then $X^-$ is absent; and when $R^2$ is present, $X^-$ is present. It is also to be understood that when $R^2$ is absent, the corresponding nitrogen atom in the piperazine ring of formula (III) lacks the depicted positive charge.

In another aspect, compounds of the invention have formula (IV),

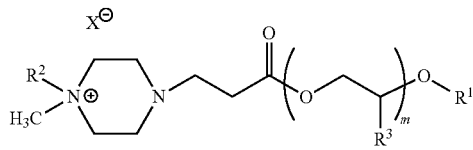

wherein $R^1$, $R^2$, $R^3$, $X^-$, and m are as defined above.

In one preferred embodiment, $R^1$ is alkyl, alkenyl, or alkynyl; $R^2$ is hydrogen, alkyl, or benzyl, or $R^2$ is absent; $R^3$ is alkyl or hydrogen; $X^-$ is a counterion or $X^-$ is absent; and m is any one of an integer from 1 to 20. In another preferred embodiment, $R^1$ is $C_1$-$C_{22}$ alkyl, or $C_1$-$C_{22}$ alkenyl; $R^2$ is $C_1$-$C_6$ alkyl, or $R^2$ is absent; $R^3$ is methyl or hydrogen; $X^-$ is bromide or chloride, or $X^-$ is absent; and m is any one of an integer from 1 to 20. In another preferred embodiment, $R^1$ is —$C_{12}H_{25}$, —$C_{18}H_{35}$, or —$C_{18}H_{37}$; $R^2$ is —$C_4H_9$ or —$C_6H_{13}$, or $R^2$ is absent; $R^3$ is H or methyl; $X^-$ is bromide or $X^-$ is absent; and m is 2, 4, 10, or 20. It is to be understood that when $R^2$ is absent, then $X^-$ is absent; and when $R^2$ is present, $X^-$ is present. It is also to be understood that when $R^2$ is absent, the corresponding nitrogen atom in the piperazine ring of formula (IV) lacks the depicted positive charge.

In another aspect, compounds of the invention have formula (V),

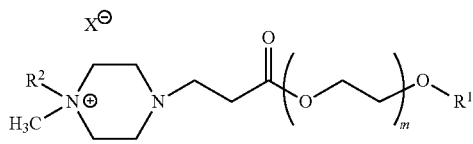

wherein $R^1$ $R^2$, $X^-$, and m are as defined above.

In one preferred embodiment, $R^1$ is alkyl, alkenyl, or alkynyl; $R^2$ is hydrogen, alkyl, or benzyl, or $R^2$ is absent; $X^-$ is a counterion or $X^-$ is absent; and m is any one of an integer from 1 to 20. In another preferred embodiment, $R^1$ is alkyl, alkenyl, or alkynyl; $R^2$ is hydrogen, alkyl, or benzyl; $X^-$ is a counterion; and m is any one of an integer from 1 to 20. In another preferred embodiment, $R^1$ is $C_1$-$C_{22}$ alkyl, or $C_1$-$C_{22}$ alkenyl; $R^2$ is $C_1$-$C_6$ alkyl; $X^-$ is bromide or chloride; and m is any one of an integer from 1 to 20. In another preferred embodiment, $R^1$ is —$C_{12}H_{25}$, —$C_{18}H_{35}$, or —$C_{18}H_{37}$; $R^2$ is —$C_4H_9$ or —$C_6H_{13}$; $X^-$ is bromide; and m is 2, 4, 10, or 20. It is to be understood that when $R^2$ is absent, then $X^-$ is absent; and when $R^2$ is present, $X^-$ is present. It is also to be understood that when $R^2$ is absent, the corresponding nitrogen atom in the piperazine ring of formula (V) lacks the depicted positive charge.

In another aspect, compounds of the invention have formula (VI),

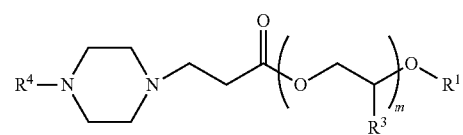

wherein $R^1$, $R^3$, $R^4$, and m are as defined above.

In one preferred embodiment, $R^1$ is alkyl, alkenyl, or alkynyl; $R^3$ is alkyl or hydrogen; $R^4$ is alkyl; and m is any one of an integer from 1 to 20. In another preferred embodiment, $R^1$ is $C_1$-$C_{22}$ alkyl, or $C_1$-$C_{22}$ alkenyl; $R^3$ is methyl or hydrogen; $R^4$ is $C_1$-$C_6$ alkyl; and m is any one of an integer from 1 to 20. In another preferred embodiment, $R^1$ is —$C_{12}H_{25}$, —$C_{18}H_{35}$, or —$C_{18}H_{37}$; $R^3$ is H or methyl; $R^4$ is methyl; and m is 2, 4, 10, or 20.

In another aspect, compounds of the invention have formula (VII), wherein

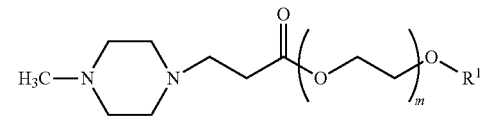

wherein $R^1$ and m are as defined above.

In one preferred embodiment, $R^1$ is alkyl, alkenyl, or alkynyl; and m is any one of an integer from 1 to 20. In another preferred embodiment, $R^1$ is $C_1$-$C_{22}$ alkyl, or $C_1$-$C_{22}$ alkenyl; and m is any one of an integer from 1 to 20. In another preferred embodiment, $R^1$ is —$C_{12}H_{25}$, —$C_{18}H_{35}$, or —$C_{18}H_{37}$; and m is 2, 4, 10, or 20.

In another aspect, compounds of the invention have formula (VIII), wherein (VIII)

wherein
$R^2$ is $C_1$-$C_{22}$ alkyl.

In one preferred embodiment, $R^2$ is unsubstituted $C_1$-$C_{22}$ alkyl. In another preferred embodiment, $R^2$ is unsubstituted straight chain $C_1$-$C_{22}$ alkyl. In another preferred embodiment, $R^2$ is unsubstituted $C_1$-$C_{10}$ alkyl. In another preferred embodiment, $R^2$ is unsubstituted straight chain $C_1$-$C_{10}$ alkyl. In another preferred embodiment, $R^2$ is unsubstituted $C_1$-$C_6$ alkyl. In another preferred embodiment, $R^2$ is unsubstituted straight chain $C_1$-$C_6$ alkyl. In another preferred embodiment, $R^2$ is unsubstituted straight chain $C_4$-$C_6$ alkyl. In another preferred embodiment, $R^2$ is —$CH_3$, —$C_2H_5$, —$C_3H_7$, —$C_4H_9$, —$C_5H_{11}$, —$C_6H_{13}$, —$C_7H_{15}$, —$C_8H_{17}$, —$C_9H_{19}$, or —$C_{10}H_{21}$. In another preferred embodiment, $R^2$ is —$C_4H_9$. In another preferred embodiment, $R^2$ is —$C_6H_{13}$. In another preferred embodiment, $R^2$ is —$CH_3$, —$CH_2CH_3$, —$(CH_2)_2CH_3$, —$(CH_2)_3CH_3$, —$(CH_2)_4CH_3$, —$(CH_2)_5CH_3$, —$(CH_2)_6CH_3$, —$(CH_2)_7CH_3$, —$(CH_2)_8CH_3$, or —$(CH_2)_9CH_3$. In another preferred embodiment, $R^2$ is —$(CH_2)_3CH_3$. In another preferred embodiment, $R^2$ is —$(CH_2)_5CH_3$.

In another aspect, compounds of the invention have formula (IX), wherein (IX)

wherein
$R^2$ is $C_5$-$C_{22}$ alkyl.

In one preferred embodiment, $R^2$ is unsubstituted $C_5$—$C_{22}$ alkyl. In another preferred embodiment, $R^2$ is unsubstituted straight chain $C_5$-$C_{22}$ alkyl. In another preferred embodiment, $R^2$ is unsubstituted $C_5$-$C_{10}$ alkyl. In another preferred embodiment, $R^2$ is unsubstituted straight chain $C_5$-$C_{10}$ alkyl. In another preferred embodiment, $R^2$ is unsubstituted $C_5$-$C_8$ alkyl. In another preferred embodiment, $R^2$ is unsubstituted straight chain $C_5$-$C_8$ alkyl. In another preferred embodiment, $R^2$ is unsubstituted straight chain $C_5$-$C_7$ alkyl. In another preferred embodiment, $R^2$ is —$C_5H_{11}$, —$C_6H_{13}$, —$C_7H_{15}$, —$C_8H_{17}$, —$C_9H_{19}$, or —$C_{10}H_{21}$. In another preferred embodiment, $R^2$ is —$C_6H_{13}$. In another preferred embodiment, $R^2$ is —$(CH_2)_4CH_3$, —$(CH_2)_5CH_3$, —$(CH_2)_6CH_3$, —$(CH_2)_7CH_3$, —$(CH_2)_8CH_3$, or —$(CH_2)_9CH_3$. In another preferred embodiment, $R^2$ is —$(CH_2)_5CH_3$.

Exemplary compounds of the invention having formula (I) include, but are not limited to:
3,6,9,12-tetraoxatetracosyl 3-(4-methylpiperazin-1-yl)propanoate;

1-butyl-1-methyl-4-(3-oxo-4,7,10,13,16-pentaoxaoctacosyl)piperazin-1-ium bromide;

1-hexyl-1-methyl-4-(3-oxo-4,7,10,13,16-pentaoxaoctacosyl)piperazin-1-ium bromide;

(Z)-2-(2-(octadec-9-enyloxy)ethoxy)ethyl 3-(4-methylpiperazin-1-yl)propanoate;

(Z)-1-butyl-1-methyl-4-(3-(2-(2-(octadec-9-enyloxy)ethoxy)ethoxy)-3-oxopropyl)piperazin-1-ium bromide;

(Z)-1-hexyl-1-methyl-4-(3-(2-(2-(octadec-9-enyloxy)ethoxy)ethoxy)-3-oxopropyl)piperazin-1-ium bromide;

3,6,9,12,15,18,21,24,27,30-decaoxaoctatetracontyl 3-(4-methylpiperazin-1-yl)propanoate;

1-butyl-1-methyl-4-(3-oxo-4,7,10,13,16,19,22,25,28,31,34-undecaoxadopentacontyl)piperazin-1-ium bromide;

1-hexyl-1-methyl-4-(3-oxo-4,7,10,13,16,19,22,25,28,31,34-undecaoxadopentacontyl)piperazin-1-ium bromide;

3,6,9,12,15,18,21,24,27,30,33,36,39,42,45,48,51,54,57,60-icosaoxaoctaheptacontyl 3-(4-methylpiperazin-1-yl)propanoate;

1-butyl-1-methyl-4-(3-oxo-4,7,10,13,16,19,22,25,28,31,34,37,40,43,46,49,52,55,58,61,64-henicosaoxadooctacontyl)piperazin-1-ium bromide;

1-hexyl-1-methyl-4-(3-oxo-4,7,10,13,16,19,22,25,28,31,34,37,40,43,46,49,52,55,58,61,64-henicosaoxadooctacontyl)piperazin-1-ium bromide;

(Z)-3,6,9,12,15,18,21,24,27,30-decaoxaoctatetracont-39-enyl 3-(4-methylpiperazin-1-yl)propanoate;

(Z)-1-butyl-1-methyl-4-(3-oxo-4,7,10,13,16,19,22,25,28,31,34-undecaoxadopentacont-43-enyl)piperazin-1-ium bromide;

(Z)-1-hexyl-1-methyl-4-(3-oxo-4,7,10,13,16,19,22,25,28,31,34-undecaoxadopentacont-43-enyl)piperazin-1-ium bromide;

(Z)-3,6,9,12,15,18,21,24,27,30,33,36,39,42,45,48,51,54,57,60-icosaoxaoctaheptacont-69-enyl 3-(4-methylpiperazin-1-yl)propanoate;

(Z)-1-butyl-1-methyl-4-(3-oxo-4,7,10,13,16,19,22,25,28,31,34,37,40,43,46,49,52,55,58,61,64-henicosaoxadooctacont-73-enyl)piperazin-1-ium bromide; and (Z)-1-hexyl-1-methyl-4-(3-oxo-4,7,10,13,16,19,22,25,28,31,34,37,40,43,46,49,52,55,58,61,64-henicosaoxadooctacont-73-enyl)piperazin-1-ium bromide.

The compounds of the invention may contain asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the scope of this invention. The present invention is meant to comprehend all such isomeric forms of these compounds.

3. Compositions

The compositions disclosed herein include at least one compound as described above. In certain embodiments, a composition of the invention contains a pure composition of a compound of formula (I). In other embodiments, a composition of the invention contains a mixture of two or more structurally distinct compounds of formula (I). In certain embodiments, a composition of the invention may comprise a mixture of compounds of formula (I), wherein one or more of $R^1$, $R^2$, $R^3$, $R^4$, $Z^a$, $Z^b$, $Z^c$, $Z^d$, $Z^e$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^a$, $R^b$, $X^-$, m, and n are variable.

In certain embodiments, a composition of the invention contains a mixture of compounds of formula (I) wherein $R^2$, $R^3$, $R^4$, $Z^a$, $Z^b$, $Z^c$, $Z^d$, $Z^e$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^a$, $R^b$, $X^-$, m, and n are the same across the compounds of formula (I) in the composition, and $R^1$ is optionally variable across the compounds of formula (I) in the composition. In certain embodiments, a composition of the invention contains a mixture of compounds of formula (I) wherein $R^1$, $R^2$, $R^3$, $R^4$, $Z^a$, $Z^b$, $Z^c$, $Z^d$, $Z^e$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^a$, $R^b$, $X^-$, and n are the same across the compounds of formula (I) in the composition, and m is optionally variable across the compounds of formula (I) in the composition. In certain embodiments, a composition of the invention contains a mixture of compounds of formula (I) wherein $R^2$, $R^3$, $R^4$, $Z^a$, $Z^b$, $Z^c$, $Z^d$, $Z^e$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^a$, $R^b$, $X^-$, and n are the same across the compounds of formula (I) in the composition, and $R^1$ and m are optionally variable across the compounds of formula (I) in the composition.

In certain embodiments, a composition of the invention contains a pure composition of a compound of formula (II), a pure composition of a compound of formula (III), a pure composition of a compound of formula (IV), a pure composition of a compound of formula (V), a pure composition of a compound of formula (VI), a pure composition of a compound of formula (VII), a pure composition of a compound of formula (VIII), a pure composition of a compound of formula (IX), or any combination thereof, wherein the variables of said formulas are as defined above.

In certain embodiments, a composition of the invention contains a mixture of compounds of formula (II), a mixture of compounds of formula (III), a mixture of compounds of formula (IV), a mixture of compounds of formula (V), a mixture of compounds of formula (VI), a mixture of compounds of formula (VII), a mixture of compounds of formula (VIII), a mixture of compounds of formula (IX), or any combination thereof, wherein the variables of said formulas are as defined above.

In certain embodiments, a composition of the invention comprises from about 1 to about 100 percent by weight of one or more compounds of the invention. In certain embodiments, a composition of the invention is a neat composition of one or more compounds of the invention.

The compositions of the invention can optionally include one or more additives. Suitable additives include, but are not limited to, synergistic compounds, asphaltene inhibitors, paraffin inhibitors, corrosion inhibitors, scale inhibitors, emulsifiers, water clarifiers, dispersants, emulsion breakers, hydrogen sulfide scavengers, gas hydrate inhibitors, biocides, pH modifiers, surfactants, and solvents.

a. Synergistic Compounds

Suitable synergistic compounds include compounds that enhance the gas hydrate inhibiting performance of the composition. In certain embodiments, the synergist compound(s) may be added to a fluid or gas simultaneously with a compound or composition of the invention, or may be added separately from a compound or composition. In certain embodiments, the synergistic compound(s) may be preblended with a compound or composition of the invention before being added to a fluid or gas to be treated.

b. Asphaltene Inhibitors

Suitable asphaltene inhibitors include, but are not limited to, aliphatic sulphonic acids; alkyl aryl sulphonic acids; aryl sulfonates; lignosulfonates; alkylphenol/aldehyde resins and similar sulfonated resins; polyolefin esters; polyolefin imides; polyolefin esters with alkyl, alkylenephenyl or alkylenepyridyl functional groups; polyolefin amides; polyolefin amides with alkyl, alkylenephenyl or alkylenepyridyl functional groups; polyolefin imides with alkyl, alkylenephenyl or alkylenepyridyl functional groups; alkenyl/vinyl pyrrolidone copolymers; graft polymers of polyolefins with maleic anhydride or vinyl imidazole; hyperbranched polyester amides; polyalkoxylated asphaltenes, amphoteric fatty acids, salts of alkyl succinates, sorbitan monooleate, and polyisobutylene succinic anhydride.

c. Paraffin Inhibitors

Suitable paraffin inhibitors include, but are not limited to, paraffin crystal modifiers, and dispersant/crystal modifier combinations. Suitable paraffin crystal modifiers include, but are not limited to, alkyl acrylate copolymers, alkyl acrylate vinylpyridine copolymers, ethylene vinyl acetate copolymers, maleic anhydride ester copolymers, branched polyethylenes, naphthalene, anthracene, microcrystalline wax and/or asphaltenes. Suitable dispersants include, but are not limited to, dodecyl benzene sulfonate, oxyalkylated alkylphenols, and oxyalkylated alkylpnenolic resins. The paraffin crystal modifiers may optionally be combined with the dispersants.

d. Corrosion Inhibitors

Suitable corrosion inhibitors include, but are not limited to, amidoamines, quaternary amines, amides, and phosphate esters.

e. Scale Inhibitors

Suitable scale inhibitors include, but are not limited to, phosphates, phosphate esters, phosphoric acids, phosphonates, phosphonic acids, polyacrylamides, salts of acrylamido-methyl propane sulfonate/acrylic acid copolymer (AMPS/AA), phosphinated maleic copolymer (PHOS/MA), and salts of a polymaleic acid/acrylic acid/acrylamido-methyl propane sulfonate terpolymer (PMA/AMPS).

f. Emulsifiers

Suitable emulsifiers include, but are not limited to, salts of carboxylic acids, products of acylation reactions between carboxylic acids or carboxylic anhydrides and amines, and alkyl, acyl and amide derivatives of saccharides (alkyl-saccharide emulsifiers).

g. Water Clarifiers

Suitable water clarifiers include, but are not limited to, inorganic metal salts such as alum, aluminum chloride, and aluminum chlorohydrate, or organic polymers such as acrylic acid based polymers, acrylamide based polymers, polymerized amines, alkanolamines, thiocarbamates, and cationic polymers such as diallyldimethylammonium chloride(DADMAC).

h. Dispersants

Suitable dispersants include, but are not limited to, aliphatic phosphonic acids with 2-50 carbons, such as hydroxyethyl diphosphonic acid, and aminoalkyl phosphonic acids, e.g. polyaminomethylene phosphonates with 2-10 N atoms e.g. each bearing at least one methylene phosphonic acid group; examples of the latter are ethylenediamine tetra(methylene phosphonate), diethylenetriamine penta(methylene phosphonate) and the triamine- and tetraminepolymethylene phosphonates with 2-4 methylene groups between each N atom, at least 2 of the numbers of methylene groups in each phosphonate being different. Other suitable dispersion agents include lignin or derivatives of lignin such as lignosulfonate and naphthalene sulfonic acid and derivatives.

i. Emulsion Breakers

Suitable emulsion breakers include, but are not limited to, dodecylbenzylsulfonic acid (DDBSA), the sodium salt of xylenesulfonic acid (NAXSA), expoxlated and propoxylated compounds, anionic cationic and nonionic surfactants, and resins, such as phenolic and epoxide resins.

j. Hydrogen Sulfide Scavengers

Suitable hydrogen sulfide scavengers include, but are not limited to, oxidants (e.g., inorganic peroxides such as sodium peroxide, or chlorine dioxide), aldehydes (e.g., of 1-10 carbons such as formaldehyde or glutaraldehyde or (meth)acrolein), triazines (e.g., monoethanol amine triazine, and monomethylamine triazine), and glyoxal.

k. Gas Hydrate Inhibitors

Suitable additional gas hydrate inhibitors include, but are not limited to, thermodynamic hydrate inhibitors (THI), kinetic hydrate inhibitors (KHI), and anti-agglomerates (AA). Suitable thermodynamic hydrate inhibitors include, but are not limited to, NaCl salt, KCl salt, $CaCl_2$ salt, $MgCl_2$ salt, $NaBr_2$ salt, formate brines (e.g. potassium formate), polyols (such as glucose, sucrose, fructose, maltose, lactose, gluconate, monoethylene glycol, diethylene glycol, triethylene glycol, mono-propylene glycol, dipropylene glycol, tripropylene glycols, tetrapropylene glycol, monobutylene glycol, dibutylene glycol, tributylene glycol, glycerol, diglycerol, triglycerol, and sugar alcohols (e.g. sorbitol, mannitol)), methanol, propanol, ethanol, glycol ethers (such as diethyleneglycol monomethylether, ethyleneglycol monobutylether), and alkyl or cyclic esters of alcohols (such as ethyl lactate, butyl lactate, methylethyl benzoate). Suitable kinetic hydrate inhibitors and anti-agglomerates include, but are not limited to, polymers and copolymers, polysaccharides (such as hydroxy-ethylcellulose (HEC), carboxymethylcellulose (CMC), starch, starch derivatives, and xanthan), lactams (such as polyvinylcaprolactam, polyvinyl lactam), pyrrolidones (such as polyvinyl pyrrolidone of various molecular weights), surfactants (such as fatty acid salts, ethoxylated alcohols, propoxylated alcohols, sorbitan esters, ethoxylated sorbitan esters, polyglycerol esters of fatty acids, alkyl glucosides, alkyl polyglucosides, alkyl sulfates, alkyl sulfonates, alkyl ester sulfonates, alkyl aromatic sulfonates, alkyl betaine, alkyl amido betaines), hydrocarbon based dispersants (such as lignosulfonates, iminodisuccinates, polyaspartates), amino acids, and proteins.

l. Biocides

Suitable biocides include, but are not limited to, oxidizing and non-oxidizing biocides. Suitable non-oxidizing biocides include, for example, aldehydes (e.g., formaldehyde, glutaraldehyde, and acrolein), amine-type compounds (e.g., quaternary amine compounds and cocodiamine), halogenated compounds (e.g., bronopol and 2-2-dibromo-3-nitrilopropionamide (DBNPA)), sulfur compounds (e.g., isothiazolone, carbamates, and metronidazole), and quaternary phosphonium salts (e.g., tetrakis(hydroxymethyl)phosphonium sulfate (THPS)). Suitable oxidizing biocides include, for example, sodium hypochlorite, trichloroisocyanuric acids, dichloroisocyanuric acid, calcium hypochlorite, lithium hypochlorite, chlorinated hydantoins, stabilized sodium hypobromite, activated sodium bromide, brominated hydantoins, chlorine dioxide, ozone, and peroxides.

m. pH Modifiers

Suitable pH modifiers include, but are not limited to, alkali hydroxides, alkali carbonates, alkali bicarbonates, alkaline earth metal hydroxides, alkaline earth metal carbonates, alkaline earth metal bicarbonates and mixtures or combinations thereof. Exemplary pH modifiers include NaOH, KOH, $Ca(OH)_2$, CaO, $Na_2CO_3$, $KHCO_3$, $K_2CO_3$, $NaHCO_3$, MgO, and $Mg(OH)_2$.

n. Surfactants

Suitable surfactants include, but are not limited to, anionic surfactants, cationic surfactants, and nonionic surfactants. Anionic surfactants include alkyl aryl sulfonates, olefin sulfonates, paraffin sulfonates, alcohol sulfates, alcohol ether sulfates, alkyl carboxylates and alkyl ether carboxylates, and alkyl and ethoxylated alkyl phosphate esters, and mono and dialkyl sulfosuccinates and sulfosuccinamates. Cationic surfactants include alkyl trimethyl quaternary ammonium salts, alkyl dimethyl benzyl quaternary ammonium salts, dialkyl dimethyl quaternary ammonium salts, and imidazolinium salts. Nonionic surfactants include alcohol alkoxylates, alkylphenol alkoxylates, block copolymers of ethylene, propylene and butylene oxides, alkyl dimethyl amine oxides, alkyl-bis(2-hydroxyethyl) amine oxides, alkyl amidopropyl dimethyl amine oxides, alkylamidopropyl-bis (2-hydroxyethyl) amine oxides, alkyl polyglucosides, polyalkoxylated glycerides, sorbitan esters and polyalkoxylated sorbitan esters, and alkoyl polyethylene glycol esters and diesters. Also included are betaines and sultanes, amphoteric surfactants such as alkyl amphoacetates and amphodiacetates, alkyl amphopropipionates and amphodipropionates, and alkyliminodiproprionate.

o. Solvents

Suitable solvents include, but are not limited to, water, isopropanol, methanol, ethanol, 2-ethylhexanol, heavy aromatic naphtha, toluene, ethylene glycol, ethylene glycol monobutyl ether (EGMBE), diethylene glycol monoethyl ether, and xylene. Representative polar solvents suitable for formulation with the composition include water, brine, seawater, alcohols (including straight chain or branched aliphatic such as methanol, ethanol, propanol, isopropanol, butanol, 2-ethylhexanol, hexanol, octanol, decanol, 2-butoxyethanol, etc.), glycols and derivatives (ethylene glycol, 1,2-propylene glycol, 1,3-propylene glycol, ethylene glycol monobutyl ether, etc.), ketones (cyclohexanone, diisobutylketone), N-methylpyrrolidinone (NMP), N,N-dimethylformamide and the like. Representative of non-polar solvents suitable for formulation with the composition include aliphatics such as pentane, hexane, cyclohexane, methylcyclohexane, heptane, decane, dodecane, diesel, and the like; aromatics such as toluene, xylene, heavy aromatic naphtha, fatty acid derivatives (acids, esters, amides), and the like.

In certain embodiments, the solvent is isopropanol, methanol, ethanol, heavy aromatic napta, toluene, ethylene glycol, ethylene glycol monobutyl ether (EGMBE), diethylene glycol monoethyl ether, xylene, kerosene, diesel, isobutanol, heptane, or a combination thereof.

In certain embodiments, a composition of the invention comprises from 0 to about 80 percent by weight of one or more solvents, based on the weight of the composition. In certain embodiments, a composition of the invention comprises from 0 to about 50 percent by weight of one or more solvents, based on the weight of the composition. In certain embodiments, a composition of the invention comprises 20%, 25%, 30%, 35%, 40%, 45%, or 50% by weight of one or more solvents, based on the weight of the composition.

p. Additional Components

Compositions made according to the invention may further include additional functional agents or additives that provide a beneficial property. Additional agents or additives will vary according to the particular composition being manufactured and its intend use as one skilled in the art will appreciate. According to one embodiment, the compositions do not contain any of the additional agents or additives.

4. Synthetic Methods

The compounds and compositions of the invention can be better understood in connection with the following synthetic schemes and methods which illustrate a means by which the compounds can be prepared.

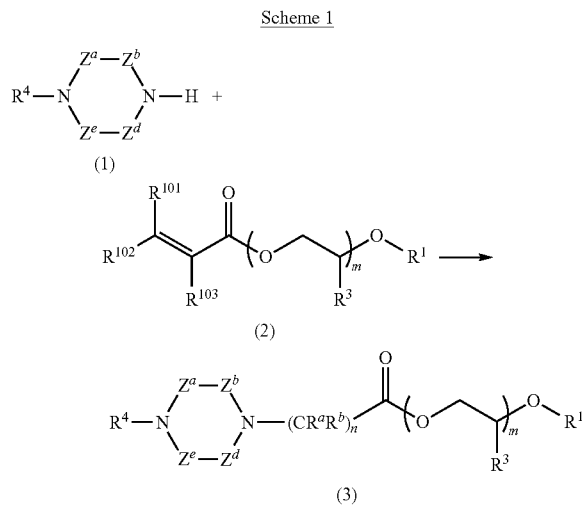

(1)

(2)

(3)

Compounds of formula (3) can be prepared as described in Scheme 1, wherein $R^1$, $R^3$, $R^4$, $Z^a$, $Z^b$, $Z^d$, $Z^e$, $R^a$, $R^b$, and m are as defined above; n is 2; and $R^{101}$, $R^{102}$, and $R^{103}$ are each independently selected from hydrogen, alkyl, alkenyl, alkynyl, aryl, heteroaryl, cycloalkyl, and heterocyclyl. Michael reaction between the compound of formula (1) and the compound of formula (2) will provide compounds of formula (3). The reaction may optionally be conducted neat or in one or more solvents, and optionally at elevated temperature (e.g., 80° C.-90° C.). Various protecting groups (e.g., esters, ethers, acetals, amides) may be used as necessary to mask other reactive functional groups that may be present in the compounds of formula (1) and formula (2).

In certain embodiments, $R^{101}$, $R^{102}$, and $R^{103}$ are each independently selected from hydrogen and alkyl. In certain embodiments, $R^{101}$, $R^{102}$, and $R^{103}$ are each independently selected from hydrogen and $C_1$-$C_6$ alkyl. In certain embodiments, $R^{101}$, $R^{102}$, and $R^{103}$ are each independently hydrogen.

In certain embodiments, $Z^a$ is $C(R^5R^6)$; $Z^b$ is $C(R^8R^9)$; $Z^d$ is $C(R^{12}R^{13})$; and $Z^e$ is $C(R^{15}R^{16})$, wherein $R^5$, $R^6$, $R^8$, $R^9$, $R^{12}$, $R^{13}$, $R^{15}$, and $R^{16}$ are as defined above. In certain embodiments, $Z^a$ is $C(R^5R^6)$; $Z^b$ is $C(R^8R^9)$; $Z^d$ is $C(R^{12}R^{13})$; and $Z^e$ is $C(R^{15}R^{16})$, wherein $R^5$, $R^6$, $R^8$, $R^9$, $R^{12}$, $R^{13}$, $R^{15}$, and $R^{16}$ are each a hydrogen atom.

In certain embodiments, $R^{101}$, $R^{102}$ and $R^{103}$ are each independently selected from hydrogen and alkyl; $Z^a$ is $C(R^5R^6)$, $Z^b$ is $C(R^8R^9)$, $Z^d$ is $C(R^{12}R^{13})$, and $Z^e$ is $C(R^{15}R^{16})$, wherein $R^5$, $R^6$, $R^8$, $R^9$, $R^{12}$, $R^{13}$, $R^{15}$, and $R^{16}$ are each a hydrogen atom; $R^1$ is alkyl or alkenyl; $R^3$ is hydrogen or alkyl; and $R^4$ is alkyl. In certain embodiments, $R^{101}$, $R^{102}$, and $R^{103}$ are each independently selected from hydrogen and $C_1$-$C_6$ alkyl; $Z^a$ is $C(R^5R^6)$, $Z^b$ is $C(R^8R^9)$ $Z^d$ is $C(R^{12}R^{13})$, and $Z^e$ is $C)R^{15}R^{16})$, wherein $R^5$, $R^6$, $R^8$, $R^9$, $R^{12}$, $R^{13}$, $R^{15}$, and $R^{16}$ are each independently a hydrogen atom; $R^1$ is $C_1$-$C_{22}$ alkyl or $C_2$-$C_{22}$ alkenyl; $R^3$ is hydrogen or methyl; and $R^4$ is methyl. In certain embodiments, $R^{101}$, $R^{102}$, and $R^{103}$, are each independently selected from hydrogen; $Z^a$ is $C(R^5R^6)$, $Z^b$ is $C(R^8R^9)$, $Z^d$ is $C(R^{12}R^{13})$, and $Z^e$ is $C(R^{15}R^{16})$, wherein $R^5$, $R^6$, $R^8$, $R^9$, $R^{12}$, $R^{13}$, $R^{15}$, and $R^{16}$ are each independently a hydrogen atom; $R^1$ is —$C_{12}H_{25}$, —$C_{18}H_{37}$, or —$C_{18}H_{35}$; $R^3$ is hydrogen; and $R^4$ is methyl.

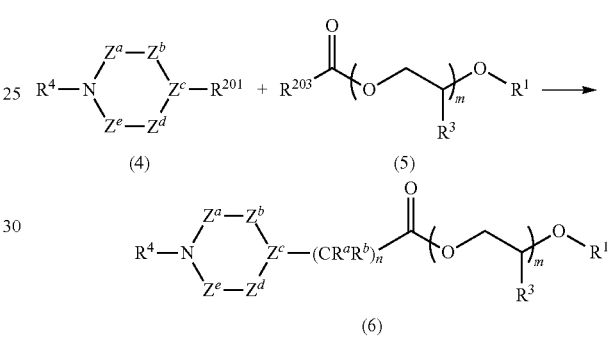

(4)     (5)

(6)

Compounds of formula (6) can be prepared as described in Scheme 2, wherein $R^1$, $R^3$, $R^4$, $Z^a$, $Z^b$, $Z^c$, $Z^d$, $Z^e$, $R^a$, $R^b$, m, and n are as defined above; and $R^{201}$ and $R^{203}$ are functional groups that may undergo coupling reactions known in the art. For example, in certain embodiments, $R^{201}$ and $R^{203}$ may be include alkenyl groups (e.g., terminal alkene groups) that can undergo cross-metathesis via an appropriate generation Grubbs or Schrock catalyst; followed by hydrogenation to provide the —$(CR^aR^b)_n$— group of the compound of formula (6). Alternatively, $R^{201}$ and $R^{203}$ may include functional groups amenable to known metal-catalyzed coupling reactions (e.g., Heck reaction, Stille coupling, etc.). Various protecting groups may be used as necessary to mask other reactive functional groups that may be present in the compounds of formula (4) and formula (5).

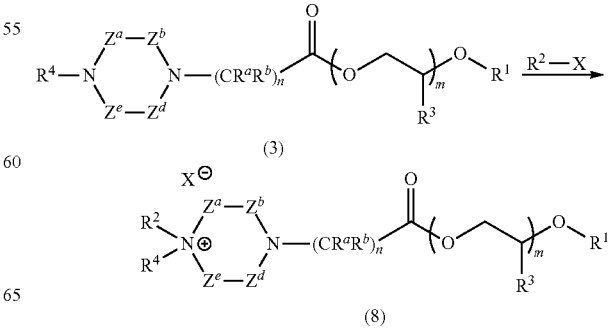

(3)

(8)

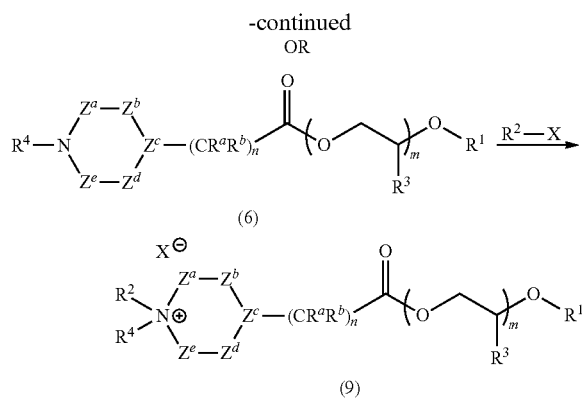

(6)

(9)

Compounds of formula (8) or compounds of formula (9) can be prepared as described in Scheme 3, wherein $R^1$, $R^2$, $R^3$, $R^4$, $Z^a$, $Z^b$, $Z^c$, $Z^d$, $Z^e$, $R^a$, $R^b$, $X^-$, m, and n are as defined above, provided that $R^2$ and $X^-$ are both present. Treatment of compounds of formula (3) or formula (6) with an electrophile of formula $R^2$—X will provide compounds of formula (8) or formula (9), wherein $R^2$ of $R^2$—X is as defined above, and X of $R^2$—X is a suitable leaving group or counterion (e.g., tosylate, mesylate, halogen). The reaction may be conducted under elevated temperature (e.g., reflux temperature) and optionally in the presence of one or more solvents (e.g., isopropanol).

Scheme 4

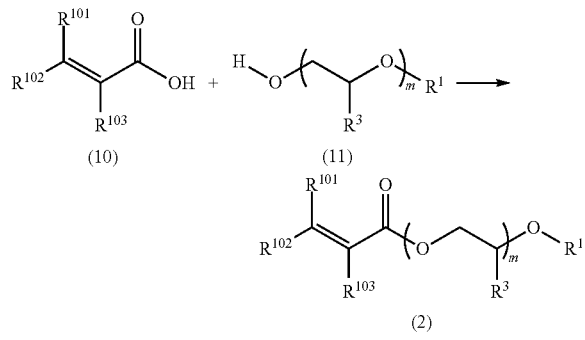

Compounds of formula (2) can be prepared as described in Scheme 4, wherein $R^1$, $R^3$, $R^{101}$, $R^{102}$, $R^{103}$, and m are as defined above. Treatment of a compound of formula (10), such as acrylic acid, with an alcohol of formula (11), such as an ethoxylated fatty alcohol, will provide compounds of formula (2) via acid catalyzed esterification. The reaction may be conducted at elevated temperature (e.g., reflux temperature, such as 90° C.), and optionally in the presence of a solvent (e.g., cyclohexane). An acid catalyst (e.g., p-toluenesulfonic acid) may be used to drive the reaction forth, as well as distillation of water by-product formed upon ester formation.

Compounds of formula (1), formula (4), and formula (5) may be commercially available, or may optionally be prepared using synthetic methodologies known to those skilled in the art.

In certain embodiments, the beta-amino ester surfactants may be further modified, for example, by manipulation of substituents. These manipulations may include, but are not limited to, reduction, oxidation, organometallic cross-coupling, alkylation, acylation, and hydrolysis reactions which are commonly known to those skilled in the art. In some cases, the order of carrying out the foregoing reaction schemes may be varied to facilitate the reaction or to avoid unwanted reaction products.

5. Product by Process

The compounds and compositions of the invention include compounds and compositions produced by a process comprising reaction, preferably Michael reaction, between a compound of formula (1) and a compound of formula (2), as described above. The compounds and compositions of the invention also include compounds and compositions produced by a process comprising reacting a compound of formula (4) with a compound of formula (5), with for example, cross-metathesis via an appropriate generation Grubbs or Schrock catalyst, followed by hydrogenation.

The products produced by the processes disclosed herein may be used neat, or prepared as compositions comprising one or more additives as described herein. The products may be used in methods of inhibiting formation of gas hydrate agglomerates, as described herein.

6. Methods of Use

The compounds and compositions of the invention may be used for inhibiting the formation of gas hydrate agglomerates. The compounds and compositions may be used to inhibit formation of gas hydrates in a fluid comprising water, gas, and optionally liquid hydrocarbon, by treating said fluid with an effective amount of a compound or composition of the invention, as described herein. The compounds and compositions of the invention can be used in any industry where it is desirable to inhibit gas hydrate agglomerates. In certain embodiments, the compounds and compositions can be applied to a gas or liquid produced or used in the production, transportation, storage, and/or separation of crude oil or natural gas.

The compounds and compositions may be added to any fluid susceptible to forming gas hydrates. A fluid to which the compounds and compositions may be introduced may be an aqueous medium. The aqueous medium may comprise water, gas, and optionally liquid hydrocarbon. A fluid to which the compounds and compositions may be introduced may be a liquid hydrocarbon. The liquid hydrocarbon may be any type of liquid hydrocarbon including, but not limited to, crude oil, heavy oil, processed residual oil, bituminous oil, coker oils, coker gas oils, fluid catalytic cracker feeds, gas oil, naphtha, fluid catalytic cracking slurry, diesel fuel, fuel oil, jet fuel, gasoline, and kerosene. In certain embodiments, the fluid or gas may be a refined hydrocarbon product. In certain embodiments, the fluid or gas may be a crude oil product.

A fluid or gas treated with a compound or composition of the invention may be at any selected temperature. A fluid or gas treated with a compound or composition of the invention may be at any selected pressure.

The compounds and compositions of the invention may be added to a fluid having various levels of water cut. For example, the water cut may be from 0% to 100% volume/volume (v/v), from 1% to 80% v/v, from 1% to 70% v/v, from 1% to 65% v/v, from 1% to 60% v/v, from 10% to 80% v/v, from 20% to 70% v/v, or from 40% to 65% v/v. The water cut may be 1% v/v, 2% v/v, 3% v/v, 4% v/v, 5% v/v, 6% v/v, 7% v/v, 8% v/v, 9% v/v, 10% v/v, 11% v/v, 12% v/v, 13% v/v, 14% v/v, 15% v/v, 16% v/v, 17% v/v, 18% v/v, 19% v/v, 20% v/v, 21% v/v, 22% v/v, 23% v/v, 24% v/v, 25% v/v, 26% v/v, 27% v/v, 28% v/v, 29% v/v, 30% v/v, 31% v/v, 32% v/v, 33% v/v, 34% v/v, 35% v/v, 36% v/v, 37% v/v, 38% v/v, 39% v/v, 40% v/v, 41% v/v, 42% v/v, 43% v/v, 44% v/v, 45% v/v, 46% v/v, 47% v/v, 48% v/v, 49% v/v, 50% v/v, 51% v/v, 52% v/v, 53% v/v, 54% v/v, 55% v/v, 56% v/v, 57% v/v, 58% v/v, 59% v/v, 60% v/v, 61% v/v, 62% v/v, 63% v/v, 64% v/v, 65% v/v, 66% v/v, 67% v/v, 68% v/v, 69% v/v, 70% v/v, 71% v/v, 72% v/v, 73% v/v, 74% v/v, 75% v/v, 76% v/v, 77% v/v, 78% v/v, 79% v/v, 80% v/v, 81% v/v, 82% v/v, 83% v/v, 84% v/v, 85% v/v, 86% v/v, 87% v/v, 88% v/v, 89% v/v, 90% v/v, 91% v/v, 92% v/v, 93% v/v, 94% v/v, 95% v/v, 96% v/v, 97% v/v, 98% v/v, 99% v/v, or 100% v/v.

The compounds and compositions of the invention may be added to a fluid having various levels of salinity. In one embodiment, the fluid may have a salinity of 0% to 25%, about 1% to 24%, 1% to 20%, or about 10% to 25% weight/weight (w/w) total dissolved solids (TDS).

The fluid or gas in which the compounds and compositions of the invention are introduced may be contained in and/or exposed to many different types of apparatuses. For example, the fluid or gas may be contained in an apparatus that transports fluid or gas from one point to another, such as an oil and/or gas pipeline. In certain embodiments, the apparatus may be part of an oil and/or gas refinery, such as a pipeline, a separation vessel, a dehydration unit, or a gas line. The fluid may be contained in and/or exposed to an apparatus used in oil extraction and/or production, such as a wellhead. The apparatus may be a cargo vessel, a storage vessel, or a holding tank. In certain embodiments, the fluid or gas may be contained in water systems, condensate/oil systems/gas systems, or any combination thereof.

The compounds or compositions of the invention may be introduced into a fluid or gas by any appropriate method for ensuring dispersal of the inhibitor through the fluid or gas. The compounds and compositions may be injected using mechanical equipment such as chemical injection pumps, piping tees, injection fittings, and the like. The compounds and compositions of the invention may be introduced with or without one or more additional polar or non-polar solvents depending upon the application and requirements. In certain embodiments, the compounds and compositions of the invention may be pumped into an oil and/or gas pipeline using an umbilical line. In certain embodiments, capillary injection systems can be used to deliver the compounds and compositions to a selected fluid. In certain embodiments, the compounds and compositions can be injected into a gas or liquid as an aqueous or nonaqueous solution, mixture, or slurry.

The compounds and compositions of the invention may be added to a fluid or gas in any amount sufficient to inhibit formation of gas hydrate agglomerates. In certain embodiments, the compounds and compositions of the invention may be applied to a fluid (e.g., a fluid contained in an oil and/or gas pipeline, well, or other apparatus) in a dose of about 0.1% volume to about 2% volume based on water cut.

The compounds and compositions may be applied to a fluid or gas at to provide any desired inhibitor concentration. Each system may have its own requirements, and may require a higher or lower dose rate of a compound or composition of the invention.

The compounds, compositions, methods, and processes of the invention will be better understood by reference to the following examples, which are intended as an illustration of and not a limitation upon the scope of the invention.

7. EXAMPLES

The foregoing may be better understood by reference to the following examples, which are presented for purposes of illustration and are not intended to limit the scope of the invention.

a. Intermediates

Intermediate 1

3,6,9,12-tetraoxatetracosyl acrylate

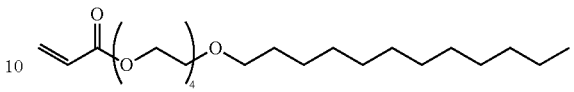

50.0 g (0.14 mole) of Brij 30 (3,6,9,12-tetraoxatetracosan-1-ol), purchased from Sigma-Aldrich, St. Louis, Mo., is charged into a 250 mL round bottom flask equipped with a distillation trap, condenser, thermocouple, and magnetic stirrer. Then, cyclohexane (40 g) and p-toluenesulfonic acid (5.2 g, 0.03 mole) are added to the reaction and the mixture is agitated using the magnetic stirrer. The temperature is adjusted to reflux (~90° C.) for 2 hours to distill any water present in the reaction mass. Acrylic acid (15.0 g, 0.21 mole) is then injected into the reactor while maintaining the reflux conditions. Water begins to distill from the reaction mass indicating the esterification reaction is proceeding as anticipated. The reaction is allowed to continue overnight and 3.3 g of water are distilled. The resulting product solution is extracted with 100 mL of saturated sodium bicarbonate to neutralize the excess acid on the reaction mass. The organic phase is separated and the solvent removed to obtain 57.4 g (0.14 mole) of product. The final product is a light yellow solid at ambient temperature. An 80% to 90% conversion of the alcohol to acrylate ester is estimated from the integration area of the olefin protons on the NMR spectra and comparing them against the methyl group from the hydrocarbon tail. $^1$H-NMR (300 MHz, CDCl$_3$): δ 6.05 (m, 1H), 5.83 (m, 1H), 5.51 (d, 9.0 Hz, 2H), 3.96 (m, 2H), 3.28 (m, 12H), 3.11 (t, 6.6 Hz, 2H), 1.25 (m, 2H), 0.98 (m, 18H), 0.56 (t, 4.4 Hz, 3H). $^{13}$C-NMR (75 MHz, CDCl$_3$): δ 164.60, 129.58, 129.13, 127.82, 127.56, 70.42, 70.38, 69.71, 69.26, 68.14, 63.42, 62.63, 31.05, 28.82, 28.78, 28.65, 28.50, 28.41, 27.79, 25.28, 25.07, 21.78, 13.16.

Intermediate 2

(Z)-2-(2-(octadec-9-enyloxy)ethoxy)ethyl acrylate

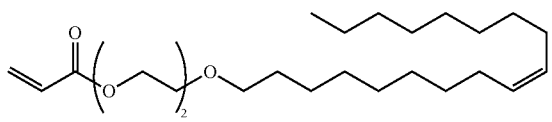

Intermediate 2 is prepared by synthetic methods described herein.

Intermediate 3

3,6,9,12,15,18,21,24,27,30-decaoxaoctatetracontyl acrylate

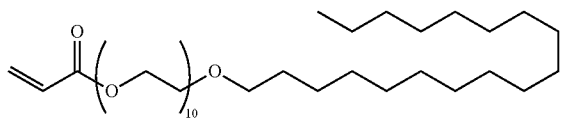

Intermediate 3 is prepared by synthetic methods described herein.

Intermediate 4

3,6,9,12,15,18,21,24,27,30,33,36,39,42,45,48,51,54,57,60-icosaoxaoctaheptacontyl acrylate

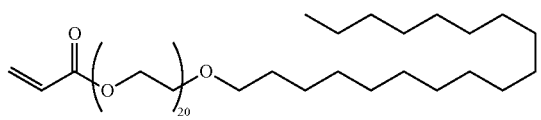

Intermediate 4 is prepared by synthetic methods described herein.

Intermediate 5

(Z)-3,6,9,12,15,18,21,24,27,30-decaoxaoctatetracont-39-enyl acrylate

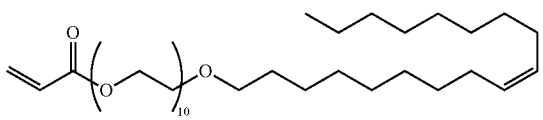

Intermediate 5 is prepared by synthetic methods described herein.

Intermediate 6

(Z)-3,6,9,12,15,18,21,24,27,30,33,36,39,42,45,48,51,54,57,60-icosaoxaoctaheptacont-69-enyl acrylate

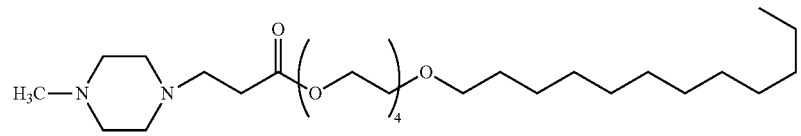

Intermediate 6 is prepared by synthetic methods described herein.

b. Beta-Amino Ester Surfactants

Example 1

3,6,9,12-tetraoxatetracosyl 3-(4-methylpiperazin-1-yl)propanoate $R^1$ is $—C_{12}H_{25}$; $R^2$ is absent; $R^3$ is H; $X^−$ is absent; m is 4

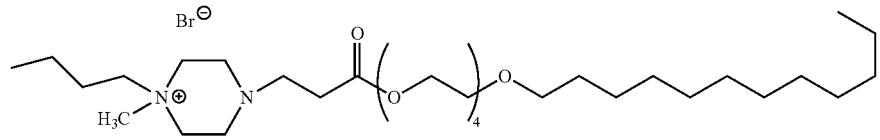

In a 250 mL round bottom flask, 26.3 g (0.063 mole) of 3,6,9,12-tetraoxatetracosyl acrylate and 6.3 g (0.063 mole) of 1-methylpiperazine are combined and agitated with a magnetic stirrer bar. The temperature is then adjusted to 85° C. and the reaction is allowed to continue overnight. The resulting product is obtained in 96% yield as a light brown liquid at ambient temperature.

Example 2

1-butyl-1-methyl-4-(3-oxo-4,7,10,13,16-pentaoxaoctacosyl)piperazin-1-ium bromide $R^1$ is $—C_{12}H_{25}$; $R^2$ is $—C_4H_9$; $R^3$ is H; $X^−$ is $Br^−$; m is 4

Example 3

1-hexyl-1-methyl-4-(3-oxo-4,7,10,13,16-pentaoxaoctacosyl)piperazin-1-ium bromide $R^1$ is —$C_{12}H_{25}$; $R^2$ is —$C_6H_{13}$; $R^3$ is H; $X^-$ is $Br^-$;
m is 4

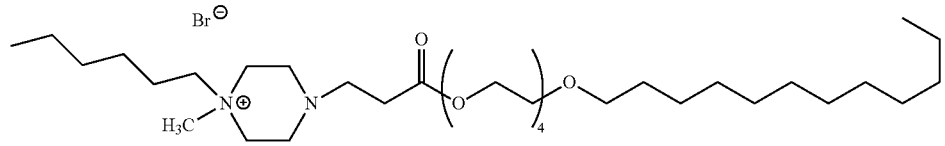

In a 100 mL round bottom flask, 10.0 g (0.019 mole) of 3,6,9,12-tetraoxatetracosyl 3-(4-methylpiperazin-1-yl)propanoate and 3.2 g (0.019 mole) of 1-bromohexane are combined with 3.3 g of isopropyl alcohol. This solution is heated to reflux overnight. After the reaction is completed, 16.5 g of methanol are added to obtain a solution with 40% active ingredient. The resulting formulation of the product is a dark brown liquid at ambient temperature. $^1$H-NMR (300 MHz, CDCl$_3$): δ 3.68 (m, 2H), 3.09 (m, 21H), 2.86 (m, 4H), 2.38 (m, 4H), 2.19 (m, 2H), 2.00 (m, 2H), 1.02 (m, 2H), 0.73 (m, 26H), 0.36 (m, 6H). $^{13}$C-NMR (75 MHz, CDCl$_3$): δ 170.50, 70.00, 69.20, 68.75, 67.69, 62.33, 62.23, 61.95, 58.91, 53.15, 51.82, 51.05, 50.32, 45.80, 45.04, 43.77, 31.06, 30.94, 30.54, 29.94, 28.34, 28.28, 28.25, 28.12, 27.96, 27.32, 24.77, 24.69, 24.59, 24.15, 21.28, 21.08, 20.63, 12.74, 12.62.

Example 4

(Z)-2-(2-(octadec-9-enyloxy)ethoxy)ethyl 3-(4-methylpiperazin-1-yl)propanoate $R^1$ is —$C_{18}H_{35}$; $R^2$ is absent; $R^3$ is H; $X^-$ is absent;
m is 2

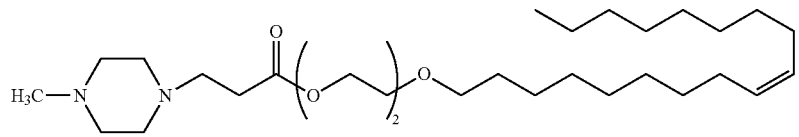

The product of Example 4 is prepared by synthetic methods described herein.

Example 5

(Z)-1-butyl-1-methyl-4-(3-(2-(2-(octadec-9-enyloxy)ethoxy)ethoxy)-3-oxopropyl)piperazin-1-ium bromide $R^1$ is —$C_{18}H_{35}$; $R^2$ is —$C_4H_9$; $R^3$ is H; $X^-$ is $Br^-$;
m is 2

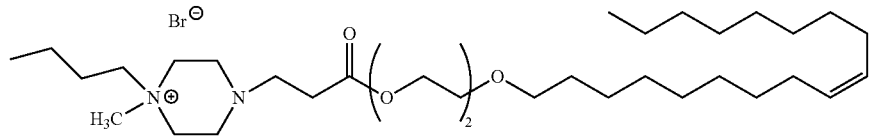

Example 6

(Z)-1-hexyl-1-methyl-4-(3-(2-(2-(octadec-9-enyloxy)ethoxy)ethoxy)-3-oxopropyl)piperazin-1-ium bromide $R^1$ is —$C_{18}H_{35}$; $R^2$ is —$C_6H_{13}$; $R^3$ is H; $X^-$ is $Br^-$; m is 2

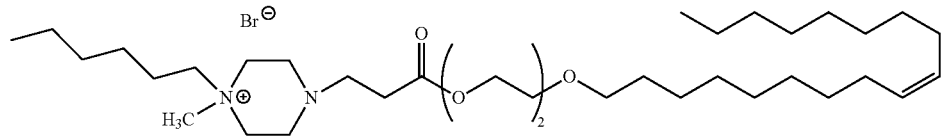

The product of Example 6 is prepared by synthetic methods described herein.

Example 7

3,6,9,12,15,18,21,24,27,30-decaoxaoctatetracontyl 3-(4-methylpiperazin-1-yl)propanoate $R^1$ is —$C_{18}H_{37}$; $R^2$ is absent; $R^3$ is H; $X^-$ is absent; m is 10

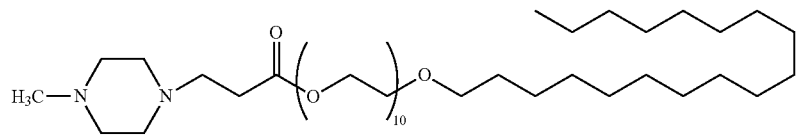

The product of Example 7 is prepared by synthetic methods described herein.

Example 8

1-butyl-1-methyl-4-(3-oxo-4,7,10,13,16,19,22,25,28,31,34-undecaoxadopentacontyl)piperazin-1-ium bromide $R^1$ is —$C_{18}H_{37}$; $R^2$ is —$C_4H_9$; $R^3$ is H; $X^-$ is $Br^-$; m is 10

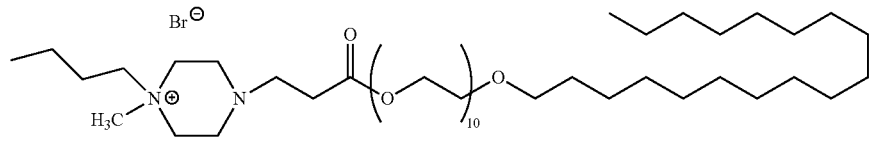

The product of Example 8 is prepared by synthetic methods described herein.

Example 9

1-hexyl-1-methyl-4-(3-oxo-4,7,10,13,16,19,22,25, 28,31,34-undecaoxadopentacontyl)piperazin-1-ium bromide $R^1$ is —$C_{18}H_{37}$; $R^2$ is —$C_6H_{13}$; $R^3$ is H; $X^-$ is $Br^-$; m is 10

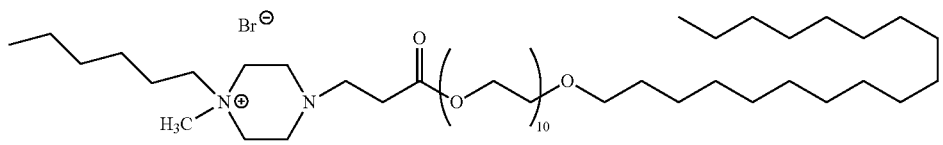

The product of Example 9 is prepared by synthetic methods described herein.

Example 10

3,6,9,12,15,18,21,24,27,30,33,36,39,42,45,48,51,54, 57,60-icosaoxaoctaheptacontyl 3-(4-methylpiperazin-1-yl)propanoate $R^1$ is —$C_{18}H_{37}$; $R^2$ is absent; $R^3$ is H; $X^-$ is absent; m is 20

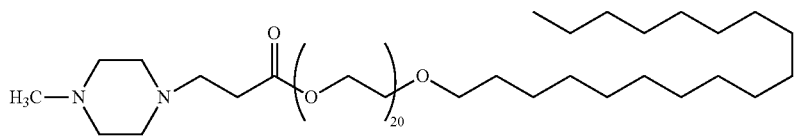

The product of Example 10 is prepared by synthetic methods described herein.

Example 11

1-butyl-1-methyl-4-(3-oxo-4,7,10,13,16,19,22,25,28, 31,34,37,40,43,46,49,52,55,58,61,64-henicosaoxadooctacontyl)piperazin-1-ium bromide $R^1$ is —$C_{18}H_{37}$; $R^2$ is —$C_4H_9$; $R^3$ is H; $X^-$ is $Br^-$, m is 20

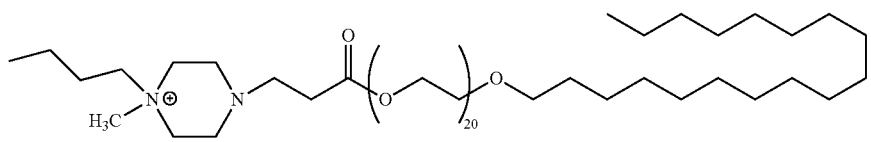

The product of Example 11 is prepared by synthetic methods described herein.

Example 12

1-hexyl-1-methyl-4-(3-oxo-4,7,10,13,16,19,22,25,
28,31,34,37,40,43,46,49,52,55,58,61,64-henic-
osaoxadooctacontyl)piperazin-1-ium bromide $R^1$ is —$C_{18}H_{37}$; $R^2$ is —$C_6H_{13}$; $R^3$ is H; $X^-$ is $Br^-$,
m is 20

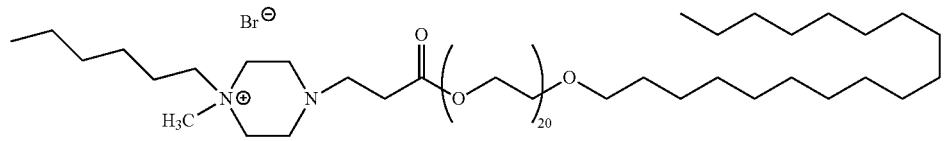

The product of Example 12 is prepared by synthetic methods described herein.

Example 13

(Z)-3,6,9,12,15,18,21,24,27,30-decaoxaoctatetra-
cont-39-enyl3-(4-methylpiperazin-1-yl)propanoate $R^1$ is —$C_{18}H_{35}$; $R^2$ is absent; $R^3$ is H; $X^-$ is absent;
m is 10

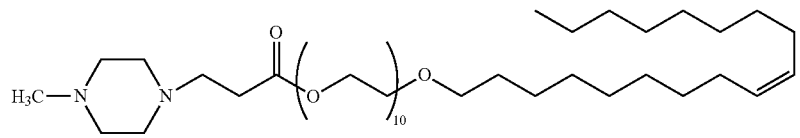

The product of Example 13 is prepared by synthetic methods described herein.

Example 14

(Z)-1-butyl-1-methyl-4-(3-oxo-4,7,10,13,16,19,22,
25,28,31,34-undecaoxadopentacont-43-enyl)piper-
azin-1-ium bromide $R^1$ is —$C_{18}H_{35}$; $R^2$ is —$C_4H_9$; $R^3$ is H; $X^-$ is $Br^-$;
m is 10

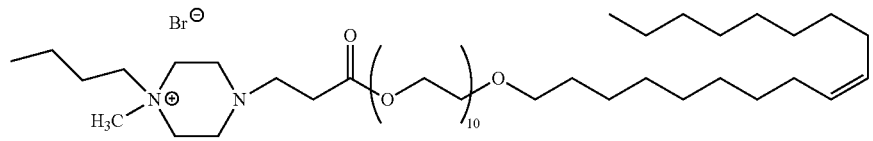

The product of Example 14 is prepared by synthetic methods described herein.

Example 15

(Z)-1-hexyl-1-methyl-4-(3-oxo-4,7,10,13,16,19,22,
25,28,31,34-undecaoxadopentacont-43-enyl)piper-
azin-1-ium bromide $R^1$ is $-C_{18}H_{35}$; $R^2$ is $-C_6H_{13}$; $R^3$ is H; $X^-$ is $Br^-$,
m is 10

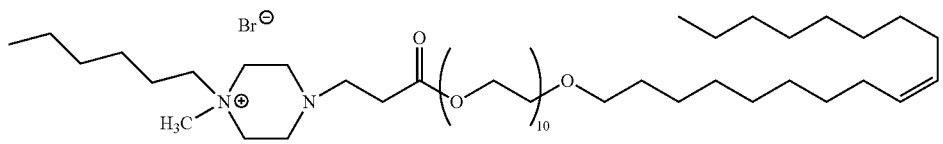

The product of Example 15 is prepared by synthetic methods described herein.

Example 16

(Z)-3,6,9,12,15,18,21,24,27,30,33,36,39,42,45,48,
51,54,57,60-icosaoxaoctaheptacont-69-enyl3-(4-
methylpiperazin-1-yl)propanoate $R^1$ is $-C_{18}H_{35}$; $R^2$ is absent; $R^3$ is H; $X^-$ is absent;
m is 20

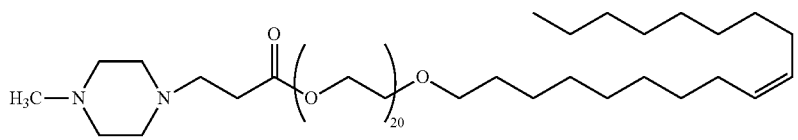

The product of Example 16 is prepared by synthetic methods described herein.

Example 17

(Z)-1-butyl-1-methyl-4-(3-oxo-4,7,10,13,16,19,22,
25,28,31,34,37,40,43,46,49,52,55,58,61,64-henic-
osaoxadooctacont-73-enyl)piperazin-1-ium bromide ($R^1$ is $-C_{18}H_{35}$; $R^2$ is $-C_4H_9$; $R^3$ is H; $X^-$ is $Br^-$,
m is 20

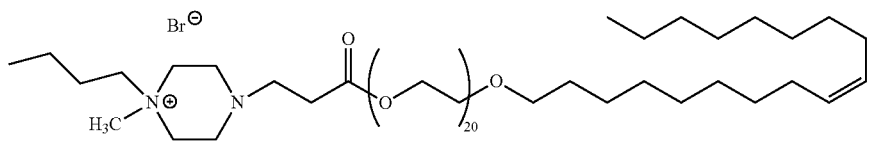

The product of Example 17 is prepared by synthetic methods described herein.

Example 18

(Z)-1-hexyl-1-methyl-4-(3-oxo-4,7,10,13,16,19,22, 25,28,31,34,37,40,43,46,49,52,55,58,61,64-henic-osaoxadooctacont-73-enyl)piperazin-1-ium bromide $R^1$ is —$C_{18}H_{35}$; $R^2$ is —$C_6H_{13}$; $R^3$ is H; $X^-$ is $Br^-$, m is 20

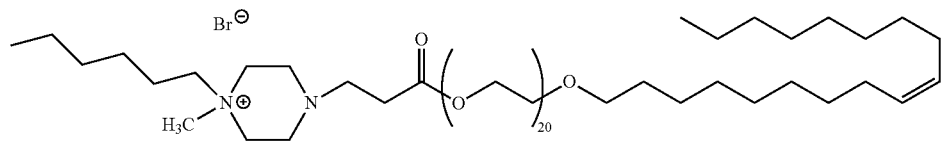

The product of Example 18 is prepared by synthetic methods described herein.

c. Anti-Agglomeration Performance

The anti-agglomeration performance for all the Examples is conducted using the Rocking Cell testing method. A Rocking Cell has two parts, a manifold and a cell body. The manifold is made up of stainless steel fittings that are welded together. It has three stems. An inlet stem is used to charge gas into the cell. An outlet stem is used to release the gas out of the cell. The third stem connects to a transducer, which measures the pressure inside of the cell. The cell body has three layers. The outer layer is a polycarbonate tube, with a thickness that is 0.7 cm. The middle layer is made of a stainless steel metal and is connected to the manifold. The inner layer contains a high-pressure sapphire tube, which has an outer diameter that is 2.8 cm, an inner diameter that is 1.85 cm, and a length that is 5 cm. This sapphire tube can handle up to 3000 psi. A stainless steel ball, which has a 1.6 cm diameter, is located inside a sapphire tube to induce turbulence and mix the fluids during the rocking process.

The test fluid usually contains three different components. For the Anti-Agglomerant test, 7.2 mL of warm magnolia crude oil is first injected into the cell. Next, 4.8 mL of a solution containing 7% by weight based upon actives of NaCl and deionized (DI) water is injected into the cell to make a 40% water cut mixture. AA chemicals are then injected into the cell. The dosage of the AA chemical is based on the amount of aqueous phase. The initial condition for the test had a temperature of 21° C. Each cell is charged by Green Canyon gas and pressurized up to 2500 psi. The cells are rocked for at least 1.5 to 2 hours until the fluid is saturated and the pressure becomes stable; then the temperature is set at 4° C. The rocking sequence is the following: cells are rocked for 16 hours (simulating steady state flowing); maintained static for 6 hours; and then rocked back for 2 hours. Pressure data is recorded during this time. Observations are taken every two or three hours before the rocking is stopped and right after the start up of the rocking test.

The AAs exemplified above are diluted in methanol (e.g., to a final concentration of 40% or 60% actives). The solutions are then dosed to obtain a final concentration of 1.5% volume of AA (based upon actives) in the aqueous phase. The mixture is charged into the rocking cell, as described above, and a stainless steel ball is added to promote mixing during the rocking part of the experiment.

Table 1 shows that the performance of a hydrate inhibitor is ranked from 1 (the worst performer) to 5 (the best) based on the following criteria:

TABLE 1

Low Dose Hydrate Inhibitor (LDHI) Rating System

| Rating | Test result | Observations |
|---|---|---|
| 1 | Fail | The rolling ball is stuck and/or the liquid level has dropped below an observable amount. |
| 2 | Fail | Large to medium agglomerates are present and/or the liquid level has dropped significantly. There is significant resistance to the rolling of the ball in the cell. |
| 3 | Marginal pass | Medium agglomerates are formed in the viewable area and/or the liquid level has dropped moderately. There is some resistance to the rolling ball in the cell. |
| 4 | Pass | Small agglomerates are formed and/or the liquid level has dropped slightly, but the solution is free flowing without hindrance. |
| 5 | Pass | Tiny and well-dispersed hydrates in the hydrocarbon phase, high liquid level, and free-flowing without hinderance. |

The testing conditions are the same for all the Examples with the exemption of increasing water cuts to determine the maximum amount of water that each chemical could tolerate. Only the examples that provided good anti-agglomeration effect at the lowest water cut of 20% or higher are described below. However, failure under the tested conditions does not necessarily indicate that the chemicals are not effective AAs because they may be able to perform under slightly different testing conditions.

Table 2 shows the results obtained from multiple Rocking Cell experiments at increasing water cuts using 1-butyl-1-methyl-4-(3-oxo-4,7,10,13,16-pentaoxaoctacosyl)piperazin-1-ium bromide (Example 2) as the gas hydrate inhibitor. At 40% water cut, 100% of the experiments passed the test of preventing agglomeration of gas hydrates. At water cuts greater than 40%, Example 2 is not effective as an anti-agglomerate chemical for the inhibition of gas hydrates.

TABLE 2

Inhibition of gas hydrate agglomeration by Example 2

| Water Cut | Dose | Number of Tests | Number of Passes | Percentage of Passes |
|---|---|---|---|---|
| 40% | 1.5% | 2 | 2 | 100% |
| 45% | 1.5% | 1 | 0 | 0% |
| 50% | 1.5% | 1 | 0 | 0% |
| 60% | 1.5% | 1 | 0 | 0% |

Table 3 presents the Rocking Cell results for 1-hexyl-1-methyl-4-(3-oxo-4,7,10,13,16-pentaoxaoctacosyl)piperazin-1-ium bromide (Example 3) at water cuts ranging from 40% to 60%. This chemical demonstrates anti-agglomeration performance at water cuts ranging from 40% to 55%.

TABLE 3

Inhibition of gas hydrate agglomeration by Example 3

| Water Cut | Dose | Number of Tests | Number of Passes | Percentage of Passes |
|---|---|---|---|---|
| 40% | 1.5% | 2 | 2 | 100% |
| 45% | 1.5% | 1 | 1 | 100% |
| 50% | 1.5% | 1 | 1 | 100% |
| 55% | 1.5% | 1 | 1 | 100% |
| 60% | 1.5% | 1 | 0 | 0% |

Table 4 presents the Rocking Cell results for (Z)-1-hexyl-1-methyl-4-(3-(2-(2-(octadec-9-enyloxy)ethoxy)ethoxy)-3-oxopropyl)piperazin-1-ium bromide (Example 6) at water cuts ranging from 40% to 70%. Example 6 is capable of preventing the agglomeration of gas hydrates at water cuts up to 65%. This chemical does not prevent agglomeration of hydrates at 70% water cut in the Rocking Cell test.

TABLE 4

Inhibition of gas hydrate agglomeration by Example 6

| Water Cut | Dose | Number of Tests | Number of Passes | Percentage of Passes |
|---|---|---|---|---|
| 40% | 1.5% | 2 | 2 | 100% |
| 45% | 1.5% | 1 | 1 | 100% |
| 50% | 1.5% | 1 | 1 | 100% |
| 55% | 1.5% | 1 | 1 | 100% |
| 60% | 1.5% | 1 | 1 | 100% |
| 65% | 1.5% | 1 | 1 | 100% |
| 70% | 1.5% | 1 | 0 | 0% |

Accordingly, compounds and compositions of the invention are effective anti-agglomerates. The compounds and compositions are particularly effective anti-agglomerates at high water (e.g., above 40%), as demonstrated by the performance of Examples 3 and 6.

Any ranges given either in absolute terms or in approximate terms are intended to encompass both, and any definitions used herein are intended to be clarifying and not limiting. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges (including all fractional and whole values) subsumed therein.

Furthermore, the invention encompasses any and all possible combinations of some or all of the various embodiments described herein. Any and all patents, patent applications, scientific papers, and other references cited in this application, as well as any references cited therein, are hereby incorporated by reference in their entirety.

What is claimed is:

1. A compound of formula (IV) or (VI),

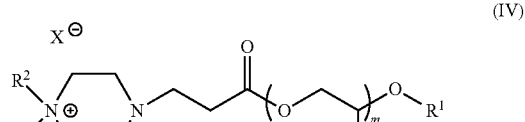

(IV)

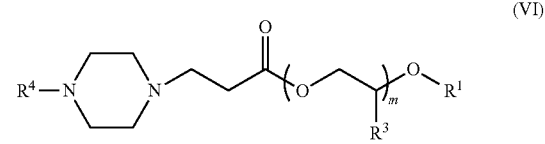

(VI)

wherein
R$^1$ is unsubstitued alkyl, or unsubstitued alkenyl;
R$^2$ is substituted or unsubstituted alkyl or substituted or unsubstituted alkenyl;
R$^3$ is hydrogen or substituted or unsubstituted alkyl;
R$^4$ is unsubstitued alkyl, or unsubstitued alkenyl;
X$^-$is a counterion;
m is any one of an integer from 1 to 100.

2. The compound of claim 1, wherein
R$^1$ is unsubstituted C$_1$-C$_{22}$ alkyl or unsubstituted C$_2$-C$_{22}$ alkenyl;
R$_2$ is hydrogen or unsubstituted C$_1$-C$_6$ alkyl;
R$^3$ is hydrogen or unsubstituted C$_1$-C$_6$ alkyl;
R$^4$ is unsubstituted C$_1$-C$_6$ alkyl; and
m is any one of an integer from 1 to 20.

3. The compound of claim 1, wherein R$^3$ is hydrogen.

4. The compound of claim 1, wherein m is 2, 4, 10, or 20.

5. The compound of claim 1, wherein R$^1$ is —C$_{12}$H$_{25}$, —C$_{18}$H$_{37}$, or —C$_{18}$H$_{35}$.

6. The compound of claim 1, having the formula (V),

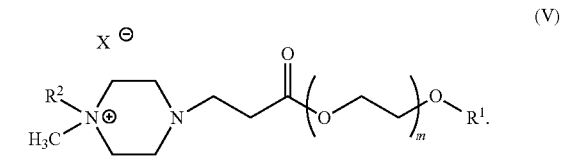

(V)

7. The compound of claim 6, wherein
R$^1$ is —(CH$_2$)$_{11}$CH$_3$, —(CH$_2$)$_{17}$CH$_3$, or —(CH$_2$)$_8$CH═CH(CH$_2$)$_7$CH$_3$;
R$^2$ is —(CH$_2$)$_3$CH$_3$, or —(CH$_2$)$_5$CH$_3$; and
X$^-$is bromide.

8. The compound of claim 7, wherein m is 2, 4, 10, or 20.

9. The compound of claim 1, selected from the group consisting of:
3,6,9,12-tetraoxatetracosyl 3-(4-methylpiperazin-1-yl)propanoate;
1-butyl-1-methyl-4-(3-oxo-4,7,10,13,16-pentaoxaoctacosyl)piperazin-1-ium bromide;
1-hexyl-1-methyl-4-(3-oxo-4,7,10,13,16-pentaoxaoctacosyl)piperazin-1-ium bromide;
(Z)-2-(2-(octadec-9-enyloxy)ethoxy)ethyl 3-(4-methylpiperazin-1-yl)propanoate;
(Z)-1-butyl-1-methyl-4-(3-(2-(2-(octadec-9-enyloxy)ethoxy)ethoxy)-3-oxopropyl)piperazin-1-ium bromide;
(Z)-1-hexyl-1-methyl-4-(3-(2-(2-(octadec-9-enyloxy)ethoxy)ethoxy)-3-oxopropyl)piperazin-1-ium bromide;

3,6,9,12,15,18,21,24,27,30-decaoxaoctatetracontyl 3-(4-methylpiperazin-1-yl)propanoate;
1-butyl-1-methyl-4-(3-oxo-4,7,10,13,16,19,22,25,28,31,34-undecaoxadopentacontyl)piperazin-1-ium bromide;
1-hexyl-1-methyl-4-(3-oxo-4,7,10,13,16,19,22,25,28,31,34-undecaoxadopentacontyl)piperazin-1-ium bromide;
3,6,9,12,15,18,21,24,27,30,33,36,39,42,45,48,51,54,57,60-icosaoxaoctaheptacontyl 3-(4-methylpiperazin-1-yl)propanoate;
1-butyl-1-methyl-4-(3-oxo-4,7,10,13,16,19,22,25,28,31,34,37,40,43,46,49,52,55,58,61,64-henicosaoxadooctacontyl)piperazin-1-ium bromide;
1-hexyl-1-methyl-4-(3-oxo-4,7,10,13,16,19,22,25,28,31,34,37,40,43,46,49,52,55,58,61,64-henicosaoxadooctacontyl)piperazin-1-ium bromide;
(Z)-3,6,9,12,15,18,21,24,27,30-decaoxaoctatetracont-39-enyl 3-(4-methylpiperazin-1-yl)propanoate;
(Z)-1-butyl-1-methyl-4-(3-oxo-4,7,10,13,16,19,22,25,28,31,34-undecaoxadopentacont-43-enyl)piperazin-1-ium bromide;
(Z)-1-hexyl-1-methyl-4-(3-oxo-4,7,10,13,16,19,22,25,28,31,34-undecaoxadopentacont-43-enyl)piperazin-1-ium bromide;
(Z)-3,6,9,12,15,18,21,24,27,30,33,36,39,42,45,48,51,54,57,60-icosaoxaoctaheptacont-69-enyl 3-(4-methylpiperazin-1-yl)propanoate;
(Z)-1-butyl-1-methyl-4-(3-oxo-4,7,10,13,16,19,22,25,28,31,34,37,40,43,46,49,52,55,58,61,64-henicosaoxadooctacont-73-enyl)piperazin-1-ium bromide; and
(Z)-1-hexyl-1-methyl-4-(3-oxo-4,10,13,16,19,22,25,28,31,34,37,40,43,46,49,52,55,58,61,64-henicosaoxadooctacont-73-enyl)piperazin-1-ium bromide.

10. The compound of claim 1, having the formula (IV)

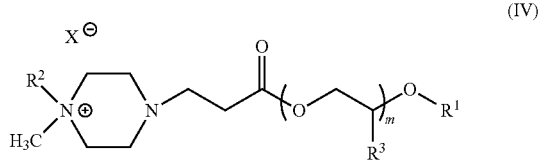

(IV)

$R^1$ is —$(CH_2)_{11}CH_3$, —$(CH_2)_{17}CH_3$, or —$(CH_2)_8CH=CH(CH_2)_7CH_3$;
$R^2$ is —$(CH_2)_3CH_3$, or —$(CH_2)_5CH_3$; and
$R^3$ is hydrogen or methyl.

11. The compound of claim 1, having the formula (VI)

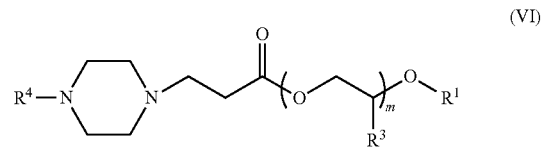

(VI)

$R^1$ is —$(CH_2)_{11}CH_3$, —$(CH_2)_{17}CH_3$, or —$(CH_2)_8CH=CH(CH_2)_7CH_3$;
$R^4$ is —$(CH_2)_3CH_3$, or —$(CH_2)_5CH_3$; and
$R^3$ is hydrogen or methyl.

12. The compound of claim 9, selected from the group consisting of:
1-butyl-1-methyl-4-(3-oxo-4,7,10,13,16-pentaoxaoctacosyl)piperazin-1-ium bromide;
1-hexyl-1-methyl-4-(3-oxo-4,7,10,13,16-pentaoxaoctacosyl)piperazin-1-ium bromide; and
(Z)-1-hexyl-1-methyl-4-(3-(2-(2-(octadec-9-enyloxy)ethoxy)ethoxy)-3-oxopropyl)piperazin-1-ium bromide.

13. A composition comprising a mixture of compounds of formula (IV) or (VI) of claim 1.

14. The composition of claim 13, further comprising one or more additives independently selected from the group consisting of a synergistic compound, an asphaltene inhibitor, a paraffin inhibitor, a corrosion inhibitor, a scale inhibitor, an emulsifier, a water clarifier, a dispersant, an emulsion breaker, a hydrogen sulfide scavenger, a gas hydrate inhibitor, a biocide, a pH modifier, a surfactant, and a solvent.

15. The composition of claim 14, comprising at least one solvent.

16. The composition of claim 15, wherein the solvent is isopropanol, methanol, ethanol, heavy aromatic naptha, toluene, ethylene glycol, ethylene glycol monobutyl ether (EGMBE), diethylene glycol monoethyl ether, xylene, kerosene, diesel, isobutanol, heptane, or a combination thereof.

17. A method of inhibiting the formation of hydrate agglomerates in a fluid comprising water, gas, and optionally liquid hydrocarbon, the method comprising adding to the fluid an effective amount of a composition comprising one or more compounds of formula (IV) or (VI) according to claim 1.

18. The method of claim 17, wherein said fluid has a salinity of 1 to 20 w/w percent total dissolved solids (TDS).

19. The method of claim 17, wherein said fluid has a water cut from 1 to 65 v/v percent.

20. The method of claim 17, wherein the fluid is contained in an oil or gas pipeline.

* * * * *

UNITED STATES PATENT AND TRADEMARK OFFICE
CERTIFICATE OF CORRECTION

PATENT NO. : 10,047,273 B2  
APPLICATION NO. : 15/111443  
DATED : August 14, 2018  
INVENTOR(S) : Erick J. Acosta and Tran-Bich Cao Page 1 of 1

It is certified that error appears in the above-identified patent and that said Letters Patent is hereby corrected as shown below:

In the Claims

Column 45, Claim 9, Line 32:  
"(Z)-1-hexyl-1-methyl-4-(3-oxo-4,10,13,16,19,22,25,28,"  
Should read:  
"(Z)-1-hexyl-1-methyl-4-(3-oxo-4,7,10,13,16,19,22,25,28,"

Signed and Sealed this  
Twenty-fifth Day of September, 2018

Andrei Iancu  
*Director of the United States Patent and Trademark Office*